US012741946B2

(12) United States Patent
Park et al.

(10) Patent No.: US 12,741,946 B2
(45) Date of Patent: Sep. 22, 2026

(54) COMPOSITION FOR PREVENTION OR TREATMENT OF NEUROFIBROMATOSIS TYPE 2 SYNDROME

(71) Applicant: PRG S&TECH INC., Busan (KR)

(72) Inventors: Bum-Joon Park, Busan (KR); Hwayoung Yun, Busan (KR)

(73) Assignee: PRG S&TECH INC., Busan (KR)

( * ) Notice: Subject to any disclaimer, the term of this patent is extended or adjusted under 35 U.S.C. 154(b) by 366 days.

(21) Appl. No.: 18/280,262

(22) PCT Filed: Jan. 24, 2022

(86) PCT No.: PCT/KR2022/001200
§ 371 (c)(1),
(2) Date: Sep. 4, 2023

(87) PCT Pub. No.: WO2022/196927
PCT Pub. Date: Sep. 22, 2022

(65) Prior Publication Data

US 2024/0092741 A1 Mar. 21, 2024

(30) Foreign Application Priority Data

Mar. 15, 2021 (KR) ........................ 10-2021-0033149

(51) Int. Cl.
*C07D 249/06* (2006.01)
*A61P 35/00* (2006.01)

(52) U.S. Cl.
CPC ............ *C07D 249/06* (2013.01); *A61P 35/00* (2018.01)

(58) Field of Classification Search
CPC ................................ C07D 249/06; A61P 35/00
(Continued)

(56) References Cited

U.S. PATENT DOCUMENTS 7,361,678 B2 4/2008 Mjalli et al.
10,723,717 B2 7/2020 Crew et al.
(Continued)

FOREIGN PATENT DOCUMENTS

CN 103159736 B 5/2015
CN 110437220 A 11/2019
(Continued)

OTHER PUBLICATIONS

Li F, Park Y, Hah JM, Ryu JS. Synthesis and biological evaluation of 1-(6-methylpyridin-2-yl)-5-(quinoxalin-6-yl)-1, 2, 3-triazoles as transforming growth factor-Î$^{2}$ type 1 receptor kinase inhibitors. Bioorganic & Medicinal Chemistry Letters. Feb. 15, 2013;23(4): 1083-6. (Year: 2013).*
(Continued)

*Primary Examiner* — Jeffrey S Lundgren
*Assistant Examiner* — Heather Dahlin
(74) *Attorney, Agent, or Firm* — Revolution IP, PLLC

(57) ABSTRACT

The present invention relates to a composition for prevention or treatment of neurofibromatosis type 2 syndrome, wherein in contrast to the conventional TβR1 kinase inhibitor TEW7197, the compound represented by chemical formula 1, a pharmaceutically acceptable salt thereof, a solvate thereof, a stereoisomer thereof, or a combination thereof according to the present invention suppresses TGF-β receptor 1 (TβR1)-mediated RKIP reduction while not inhibiting normal TGF-β signaling and thus, can be used as a novel form of a therapeutic agent for neurofibromatosis type 2 syndrome, which can solve the side effect problem caused by the inhibition of normal TGF-β signaling.

5 Claims, 18 Drawing Sheets

Specification includes a Sequence Listing.

(58) Field of Classification Search
USPC .......................................................... 514/359
See application file for complete search history.

(56) References Cited

U.S. PATENT DOCUMENTS

| | | | | |
|---|---|---|---|---|
| 2007/0173530 | A1* | 7/2007 | deLong et al. | .... A61K 31/4709 514/307 |
| 2014/0163026 | A1 | 6/2014 | Campbell et al. | |

FOREIGN PATENT DOCUMENTS

| | | | |
|---|---|---|---|
| JP | 2005-525378 | A | 8/2005 |
| JP | 2010-515739 | A | 5/2010 |
| JP | 2016-135778 | A | 7/2016 |
| KR | 10-2014-0040715 | A | 4/2014 |
| KR | 10-1924018 | B1 | 11/2018 |
| WO | 2012-145503 | A1 | 10/2012 |
| WO | 2019-204505 | A2 | 10/2019 |
| WO | 2020-123453 | A2 | 6/2020 |

OTHER PUBLICATIONS

International Search Report for PCT/KR2022/001200 mailed May 4, 2022 from Korean Intellectual Property Office.

Jung-Hyun Cho et al., "Loss of NF2 Induces TGFB Receptor 1-mediated Noncanonical and Oncogenic TGFβ Signaling: Implication of the Therapeutic Effect of TGFβ Receptor 1 Inhibitor on NF2 Syndrome", Molecular cancer therapeutics, vol. 17, Issue No. 11, Nov. 2019, pp. 2271-2284.

* cited by examiner

[FIG. 1]
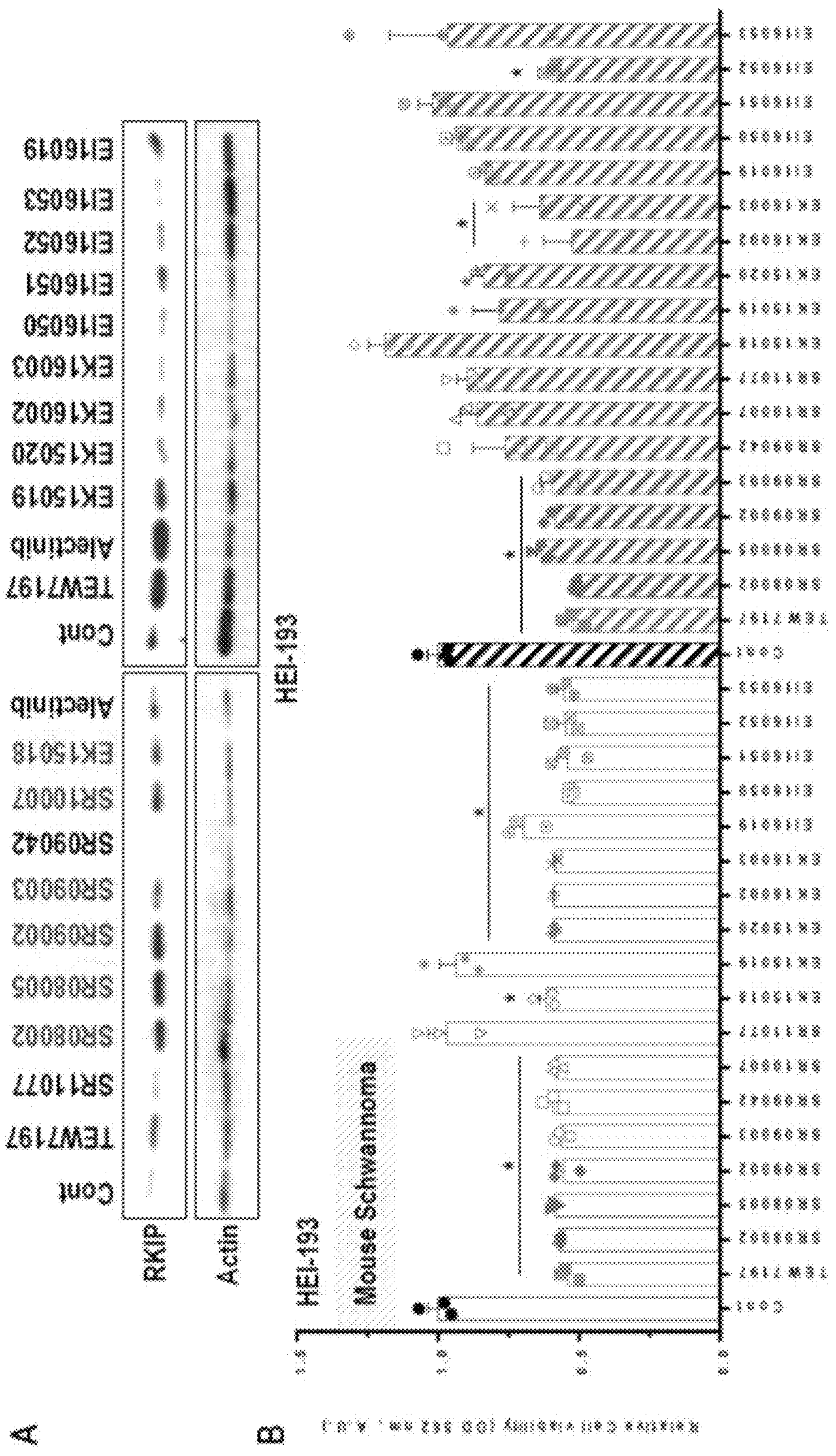

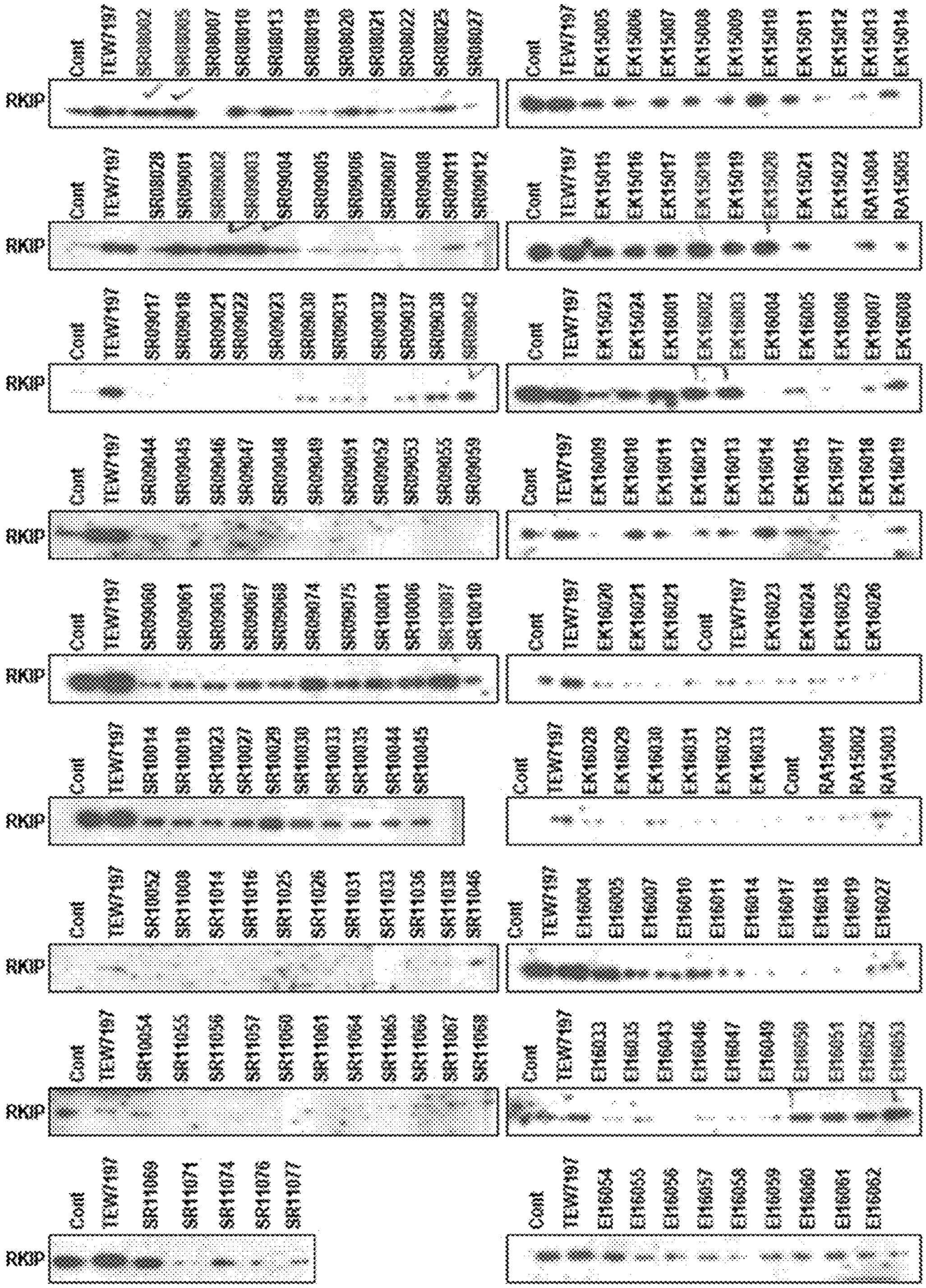
[FIG. 2]

[FIG. 3]
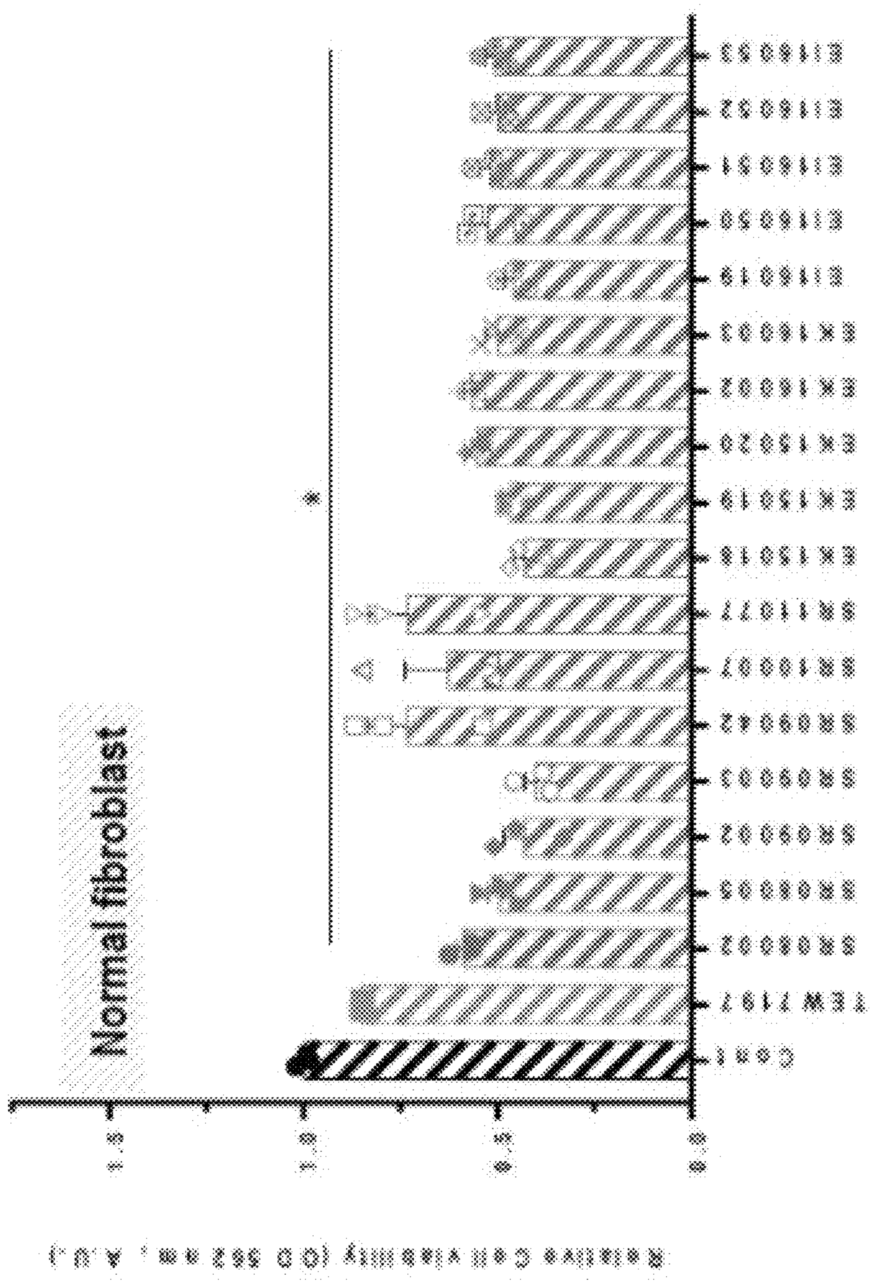

[FIG. 4]
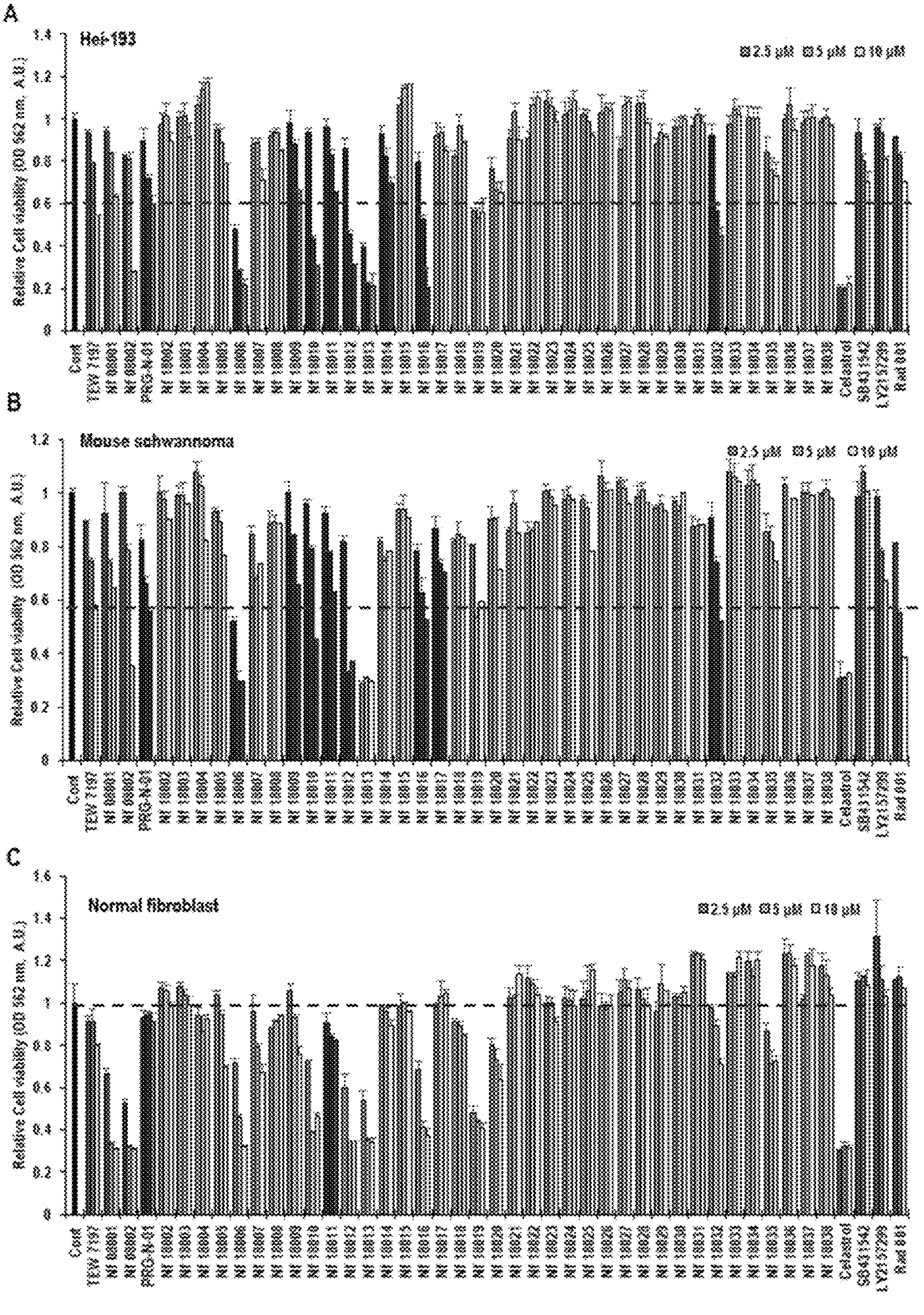

[FIG. 5]
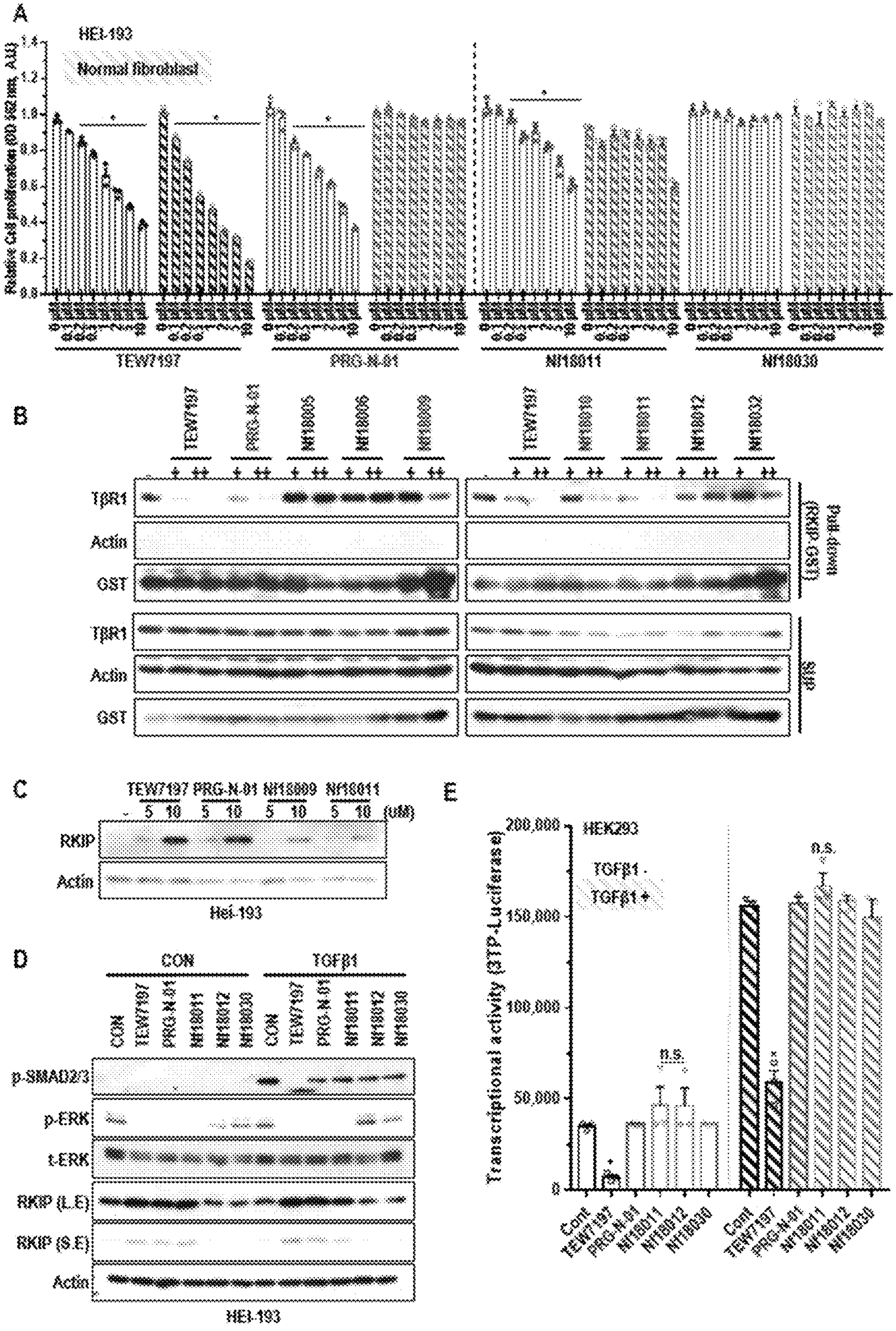

[FIG. 6]
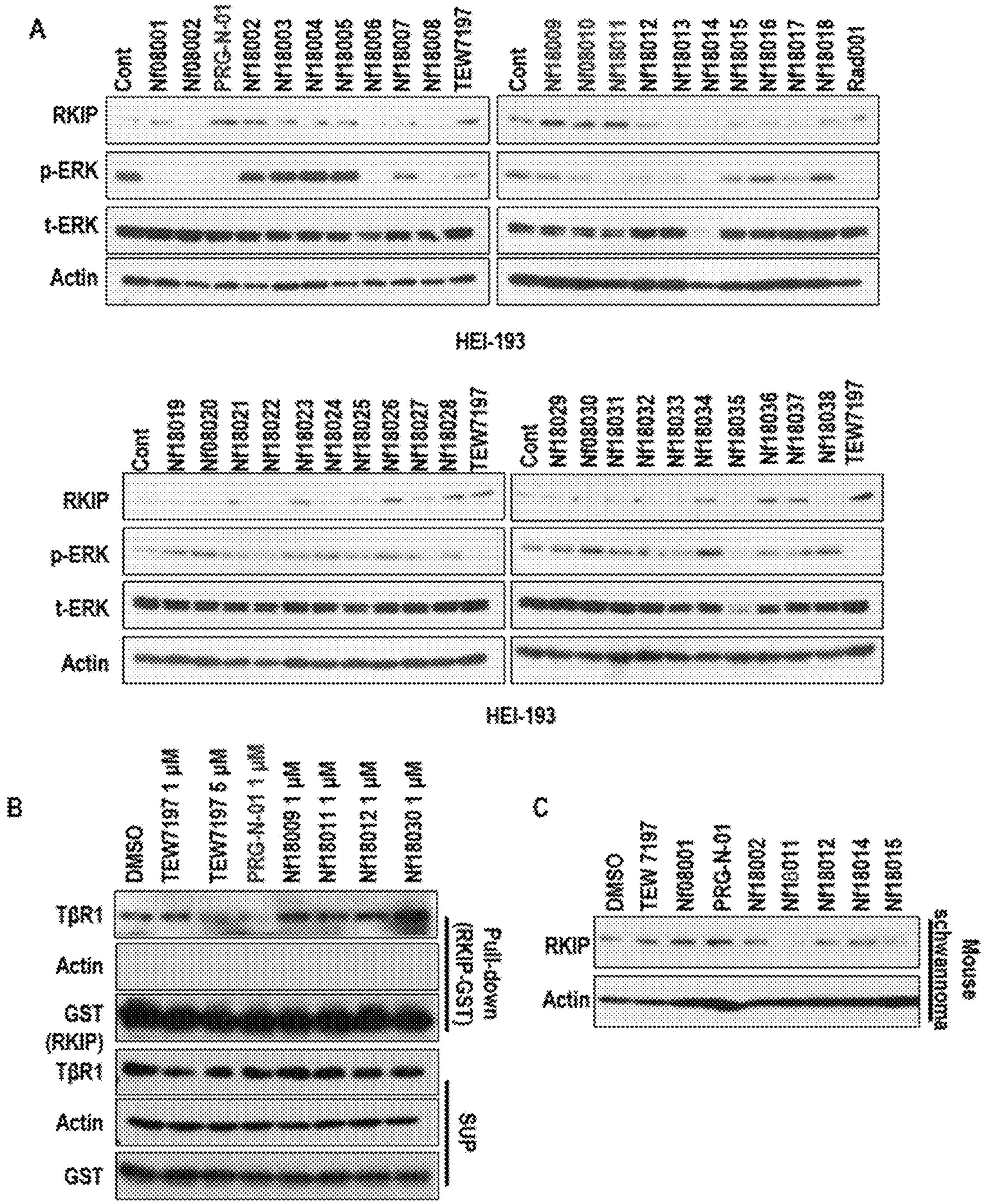

[FIG. 7]
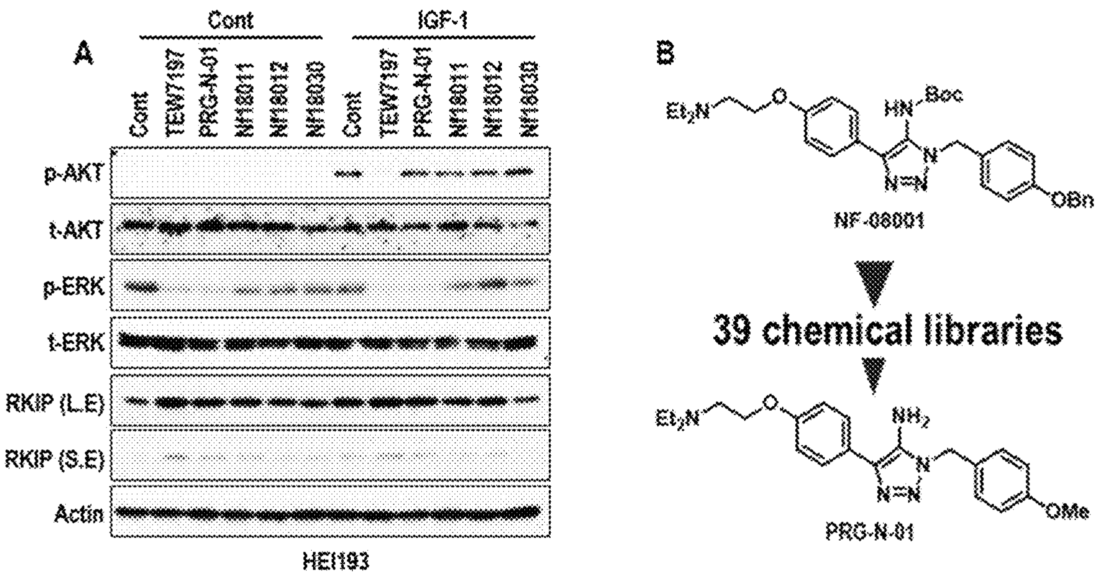
NF-08001
PRG-N-01

[FIG. 8]
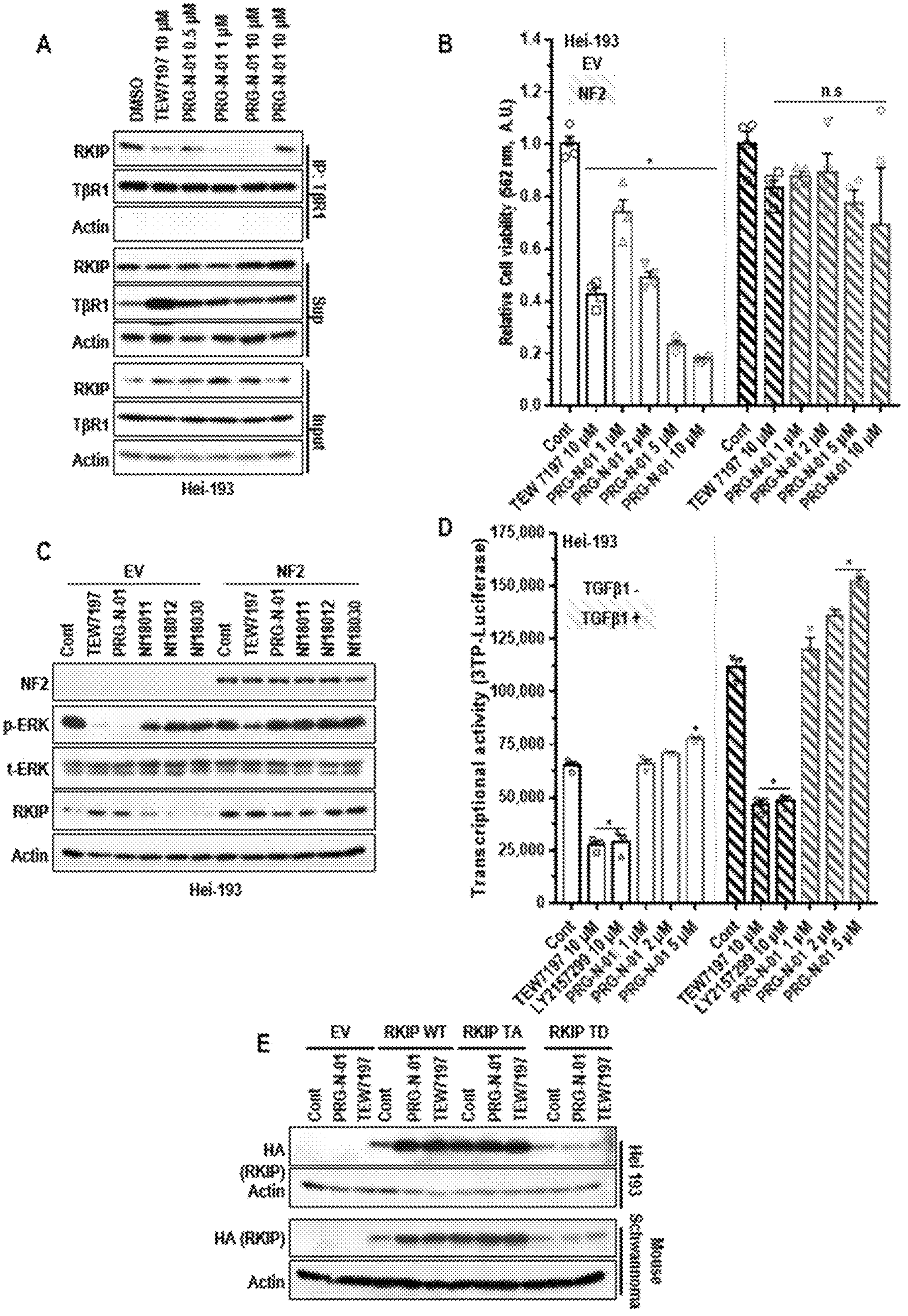

[FIG. 9]
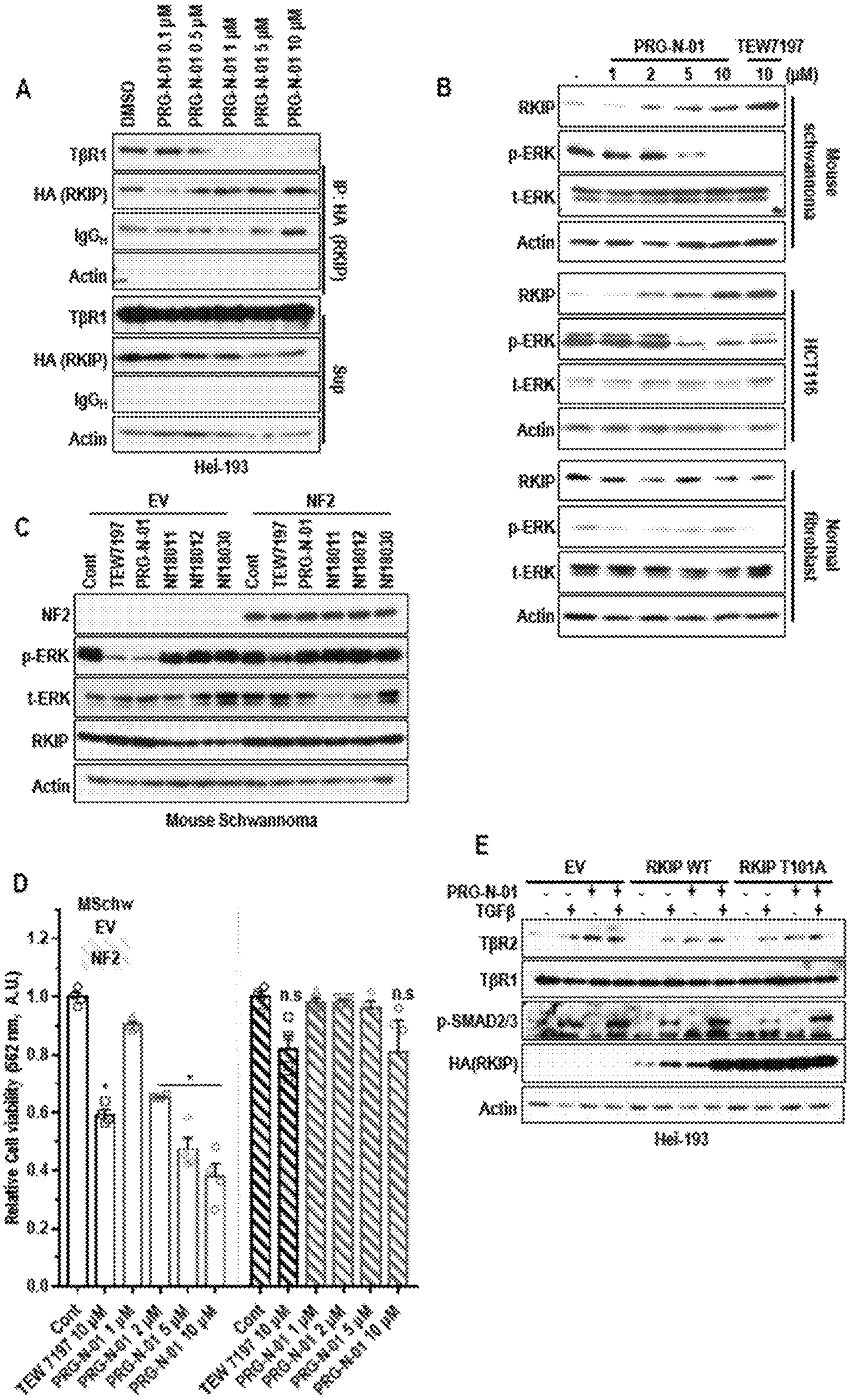

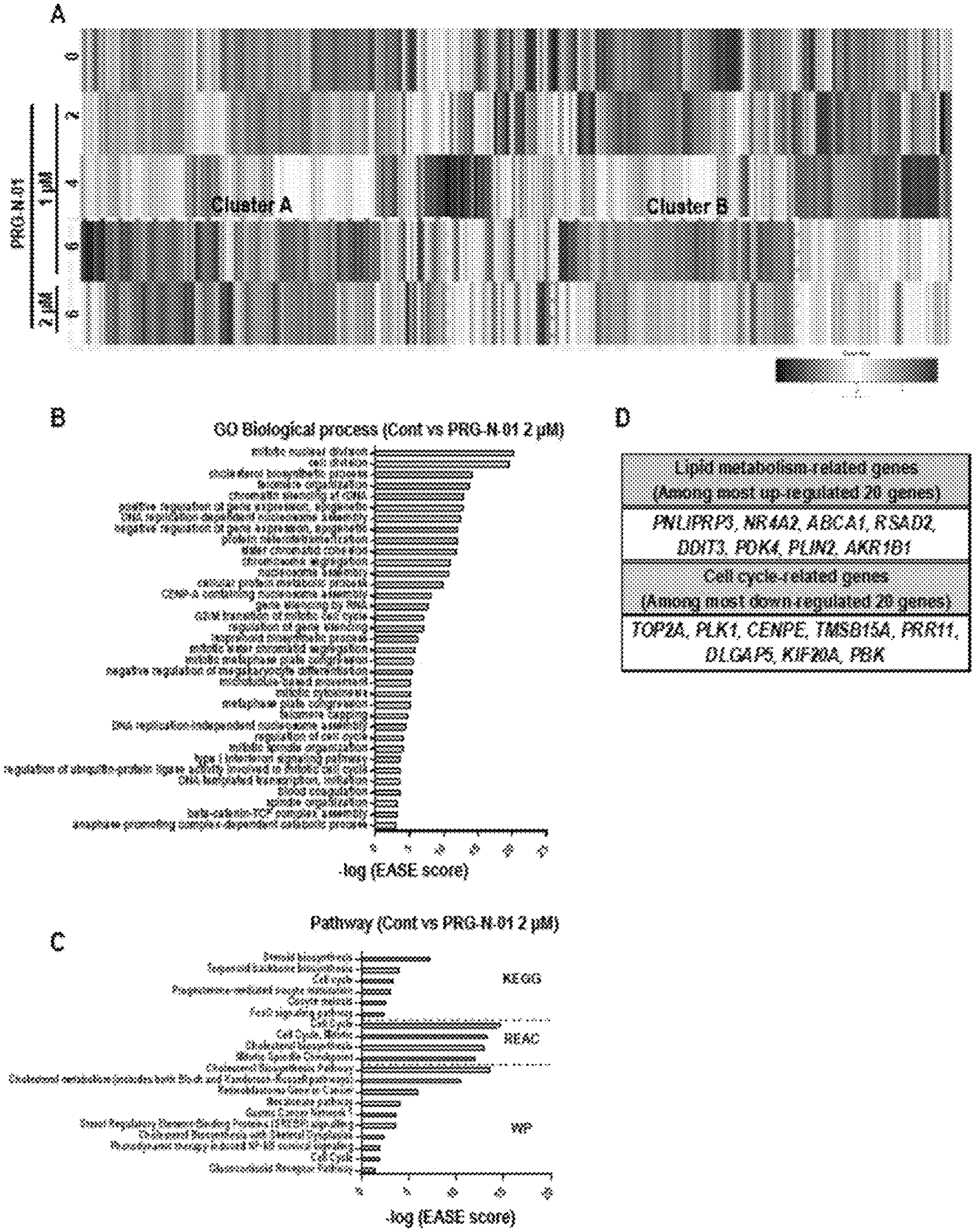
[FIG. 10]
A
B
C
D
| Lipid metabolism-related genes (Among most up-regulated 20 genes) |
| --- |
| *PNLIPRP3, NR4A2, ABCA1, RSAD2, DDIT3, PDK4, PLIN2, AKR1B1* |
| Cell cycle-related genes (Among most down-regulated 20 genes) |
| *TOP2A, PLK1, CENPE, TMSB15A, PRR11, DLGAP5, KIF20A, PBK* |

[FIG. 11]
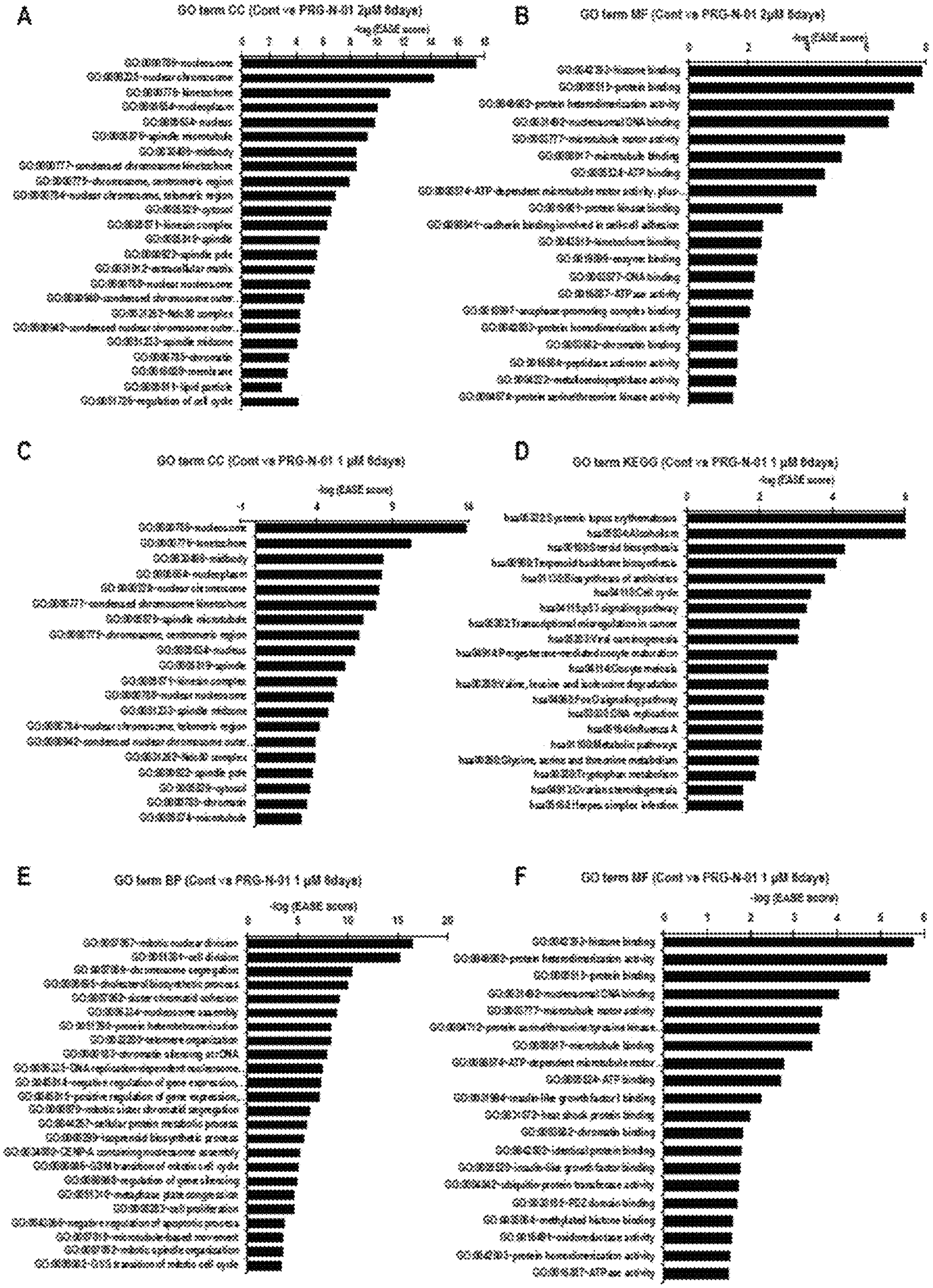

[FIG. 12]
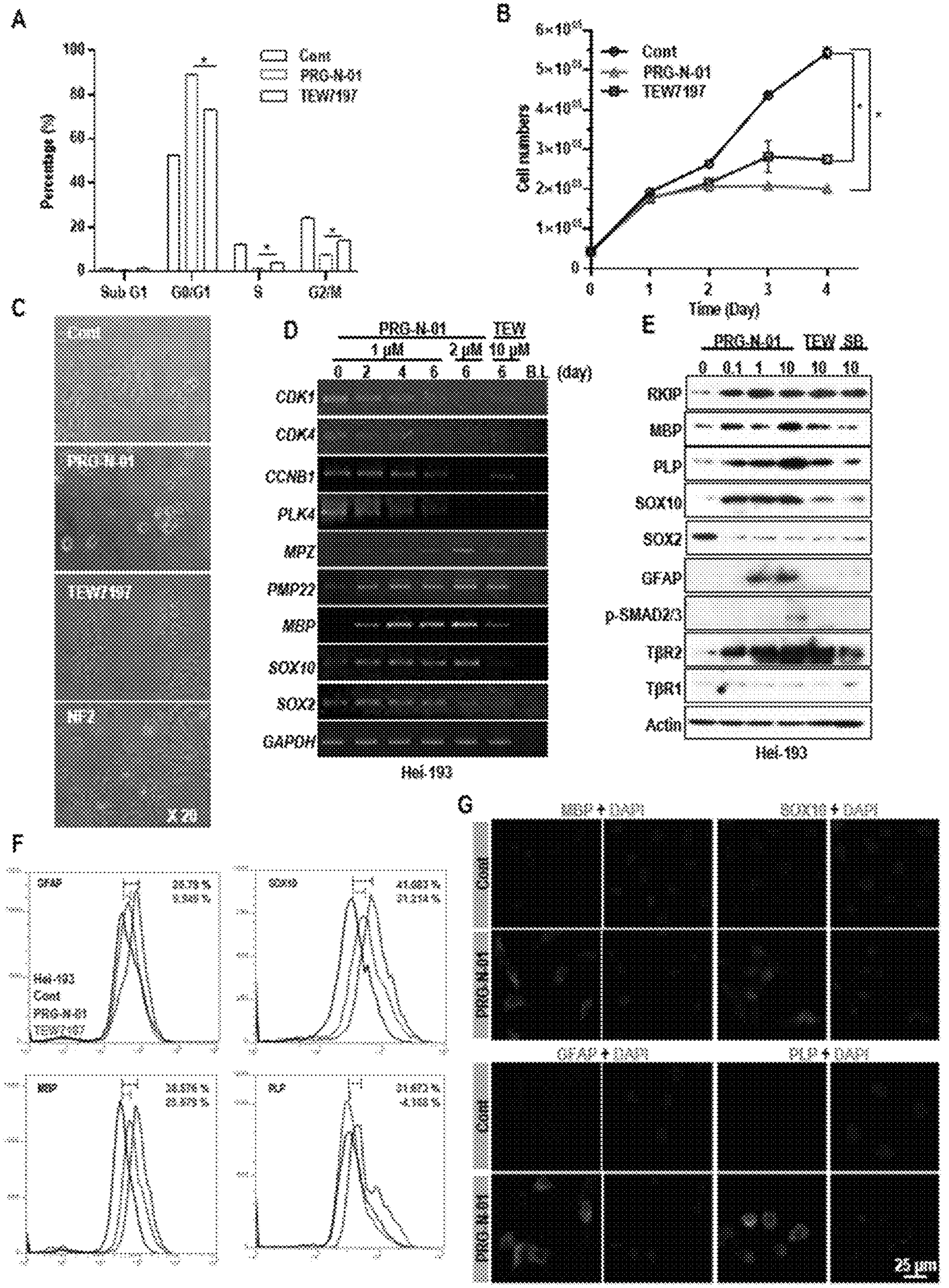

[FIG. 13]
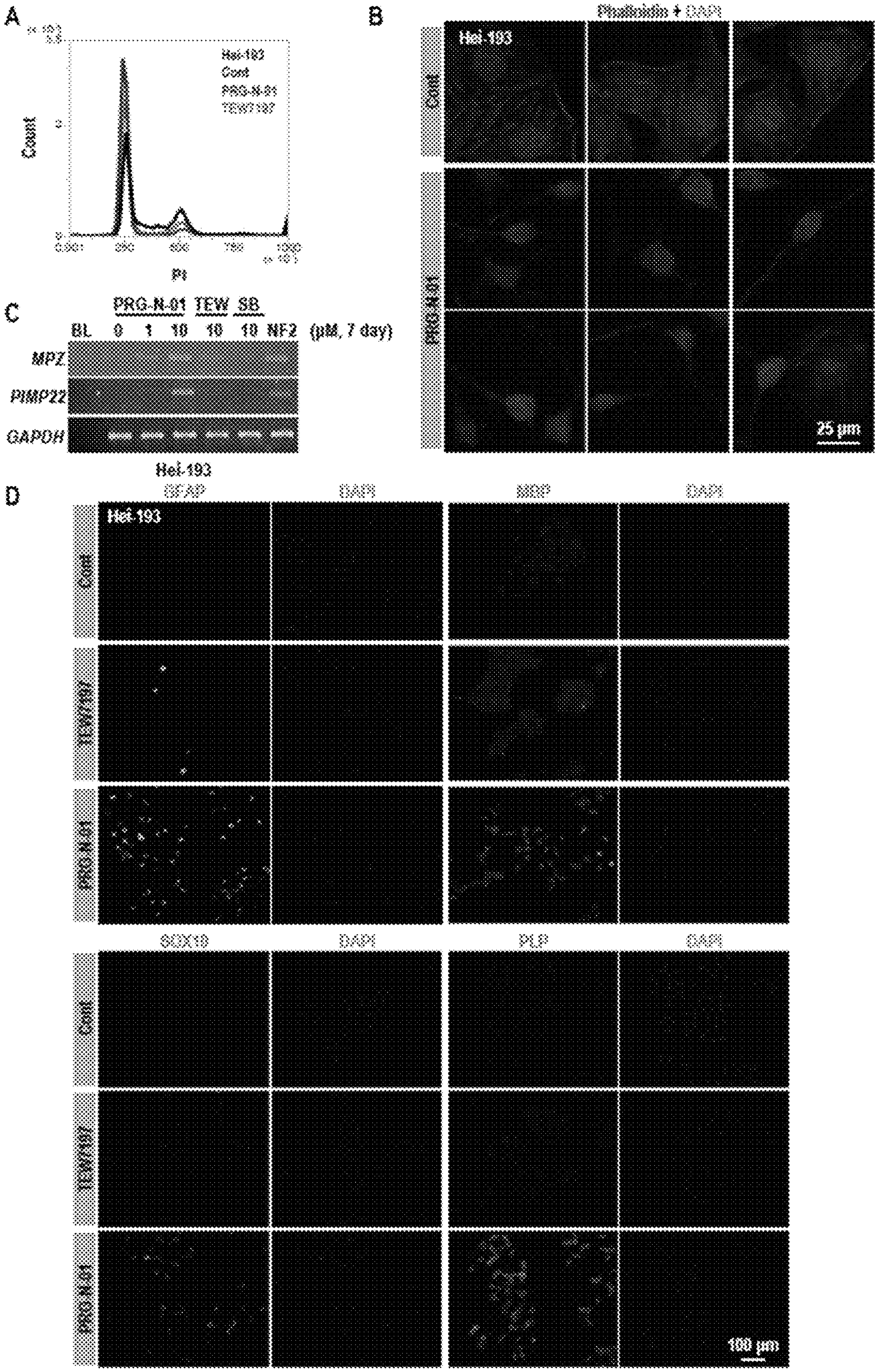

[FIG. 14]
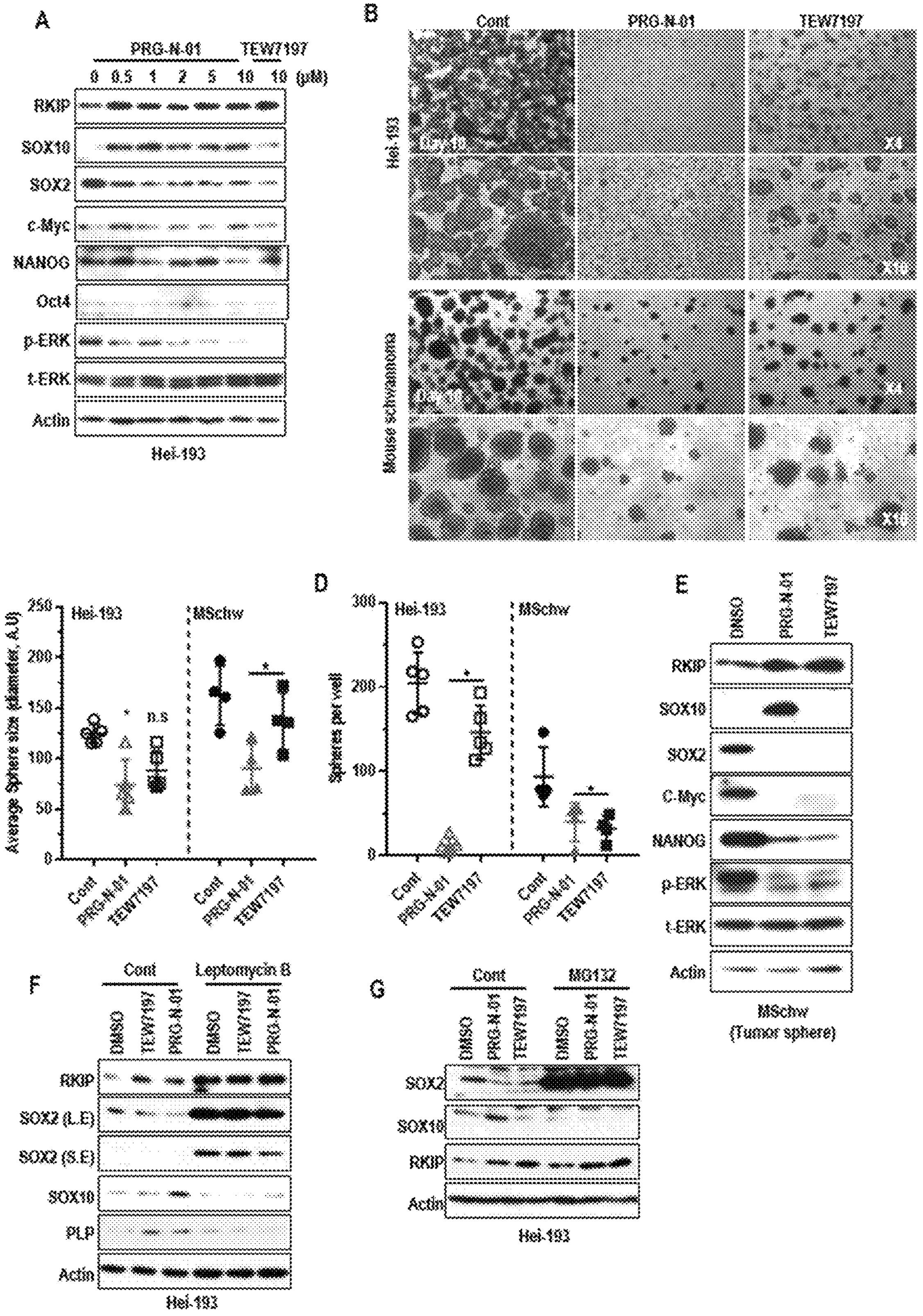

[FIG. 15]
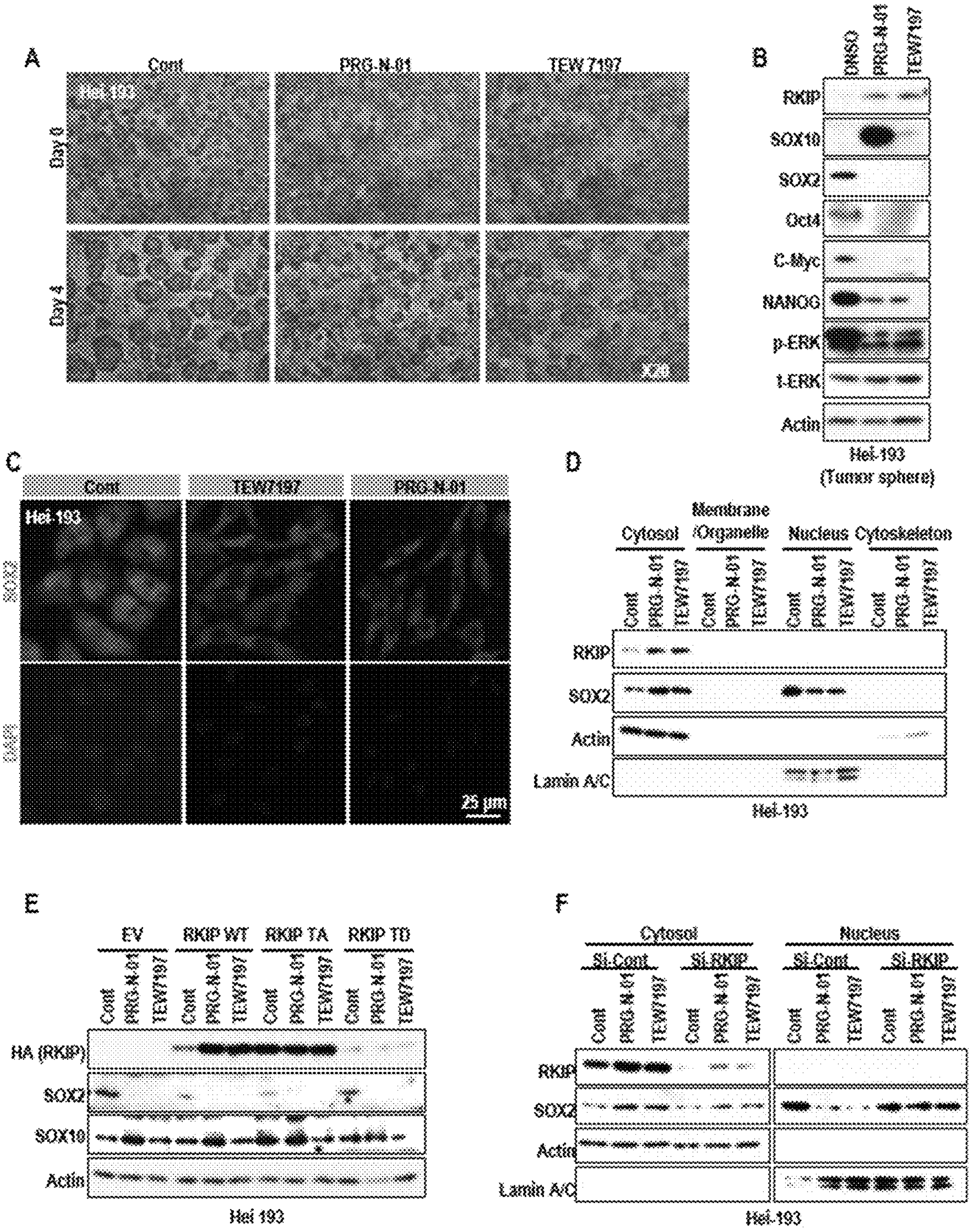

[FIG. 16]
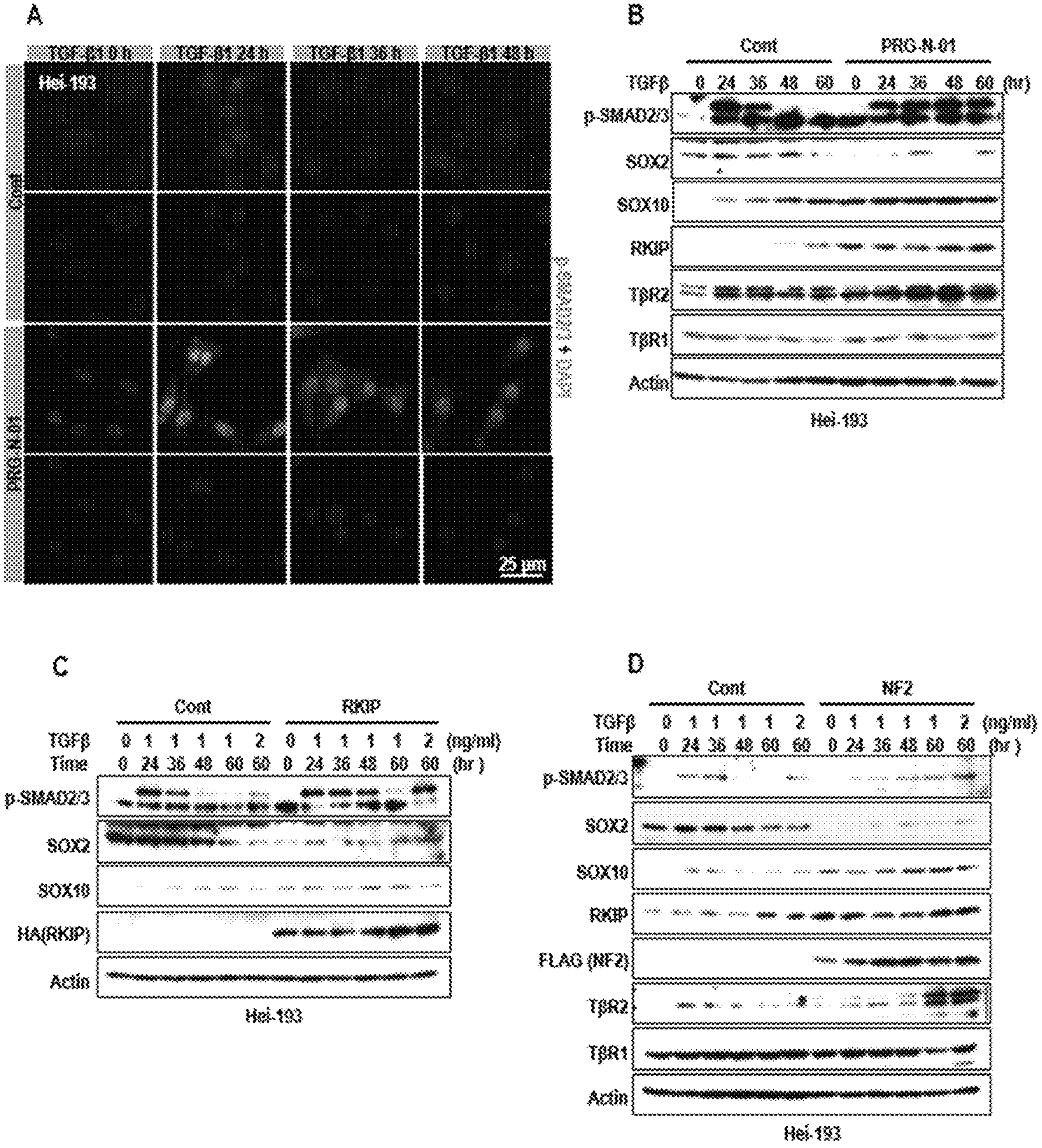

[FIG. 17]
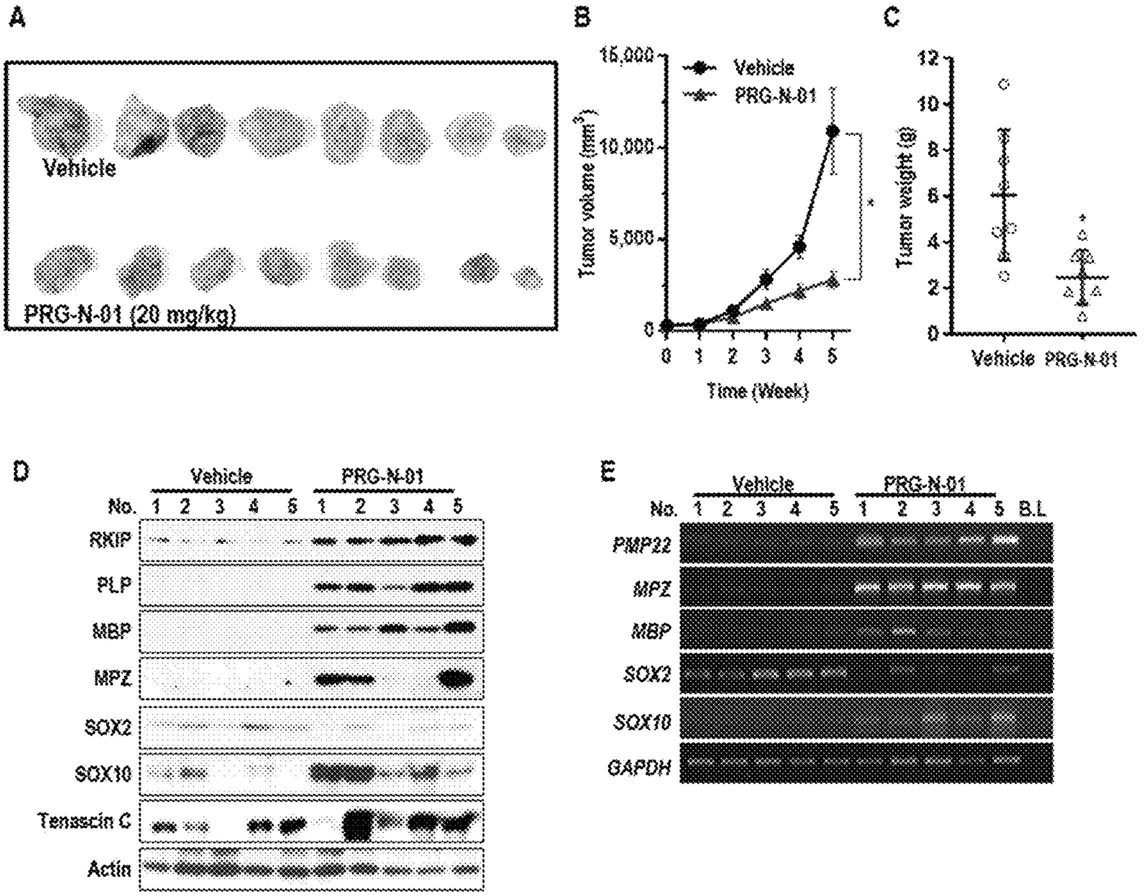

[FIG. 18]
A
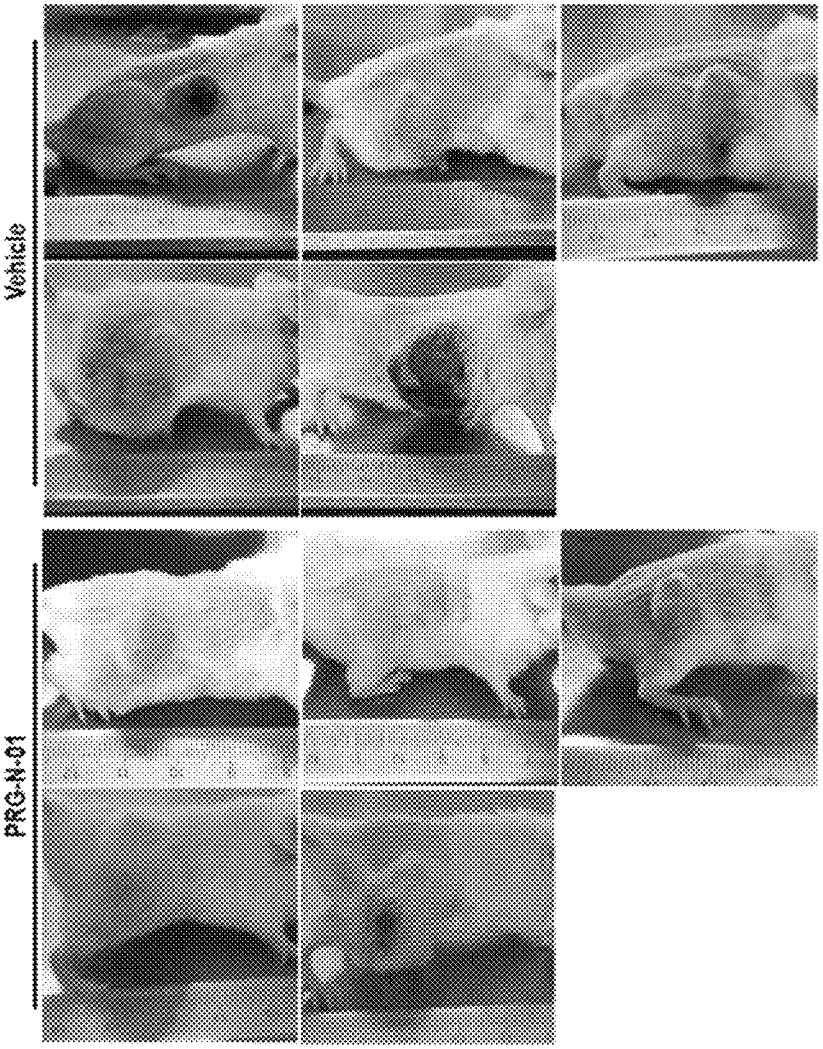
B
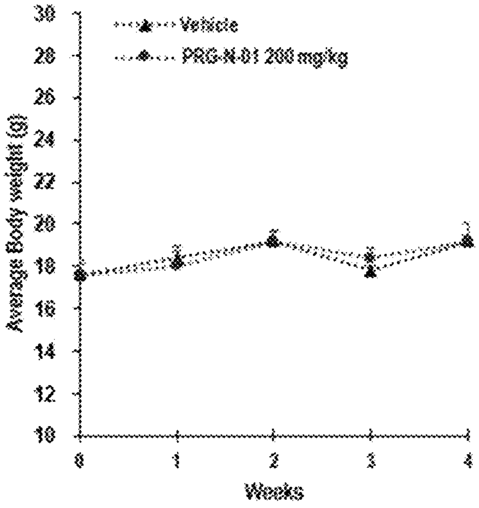

COMPOSITION FOR PREVENTION OR TREATMENT OF NEUROFIBROMATOSIS TYPE 2 SYNDROME

CROSS REFERENCE TO PRIOR APPLICATIONS

This application is a National Stage Application of PCT International Patent Application No. PCT/KR2022/001200 filed on Jan. 24, 2022, under 35 U.S.C. § 371, which claims priority to Korean Patent Application No. 10-2021-0033149 filed Mar. 15, 2021, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF-2280-465_ST25.txt, created on Sep. 3, 2023, and 4,297 bytes in size.

TECHNICAL FIELD

The present disclosure relates to a novel compound that inhibits TGF-β receptor 1 (TβR1)-mediated RKIP reduction without interfering with normal TGF-β signaling and a composition for preventing or treating neurofibromatosis type 2 (NF2) syndrome including the same.

BACKGROUND ART

Neurofibromatosis (NF) is a genetic disorder that affects bones, soft tissues, skin, and nervous system and classified into neurofibromatosis type 1 (NF1) and neurofibromatosis type 2 (NF2). Neurofibromatosis type 2 is a benign tumor developing in the cranial nerve, the eighth nerve, accompanied with symptoms such as hearing loss, tinnitus, and balance disorders, and is also called vestibular schwannomas because it occurs in schwann cells in the central nervous system. The average age at which neurofibromatosis type 2 develops ranges from 18 to 24 years, and it is known that bilateral vestibular schwannoma occurs in almost all patients by the age of 30. In addition, progression of schwannomas such as tumors in cranial nerves and peripheral nerves, meningioma, ependymoma, and, very rarely, astrocytoma may occur.

The neurofibromatosis type 2 is caused by mutation in an NF2 gene, which is located on a long arm of chromosome 22 (22q12.2). The NF2 gene is responsible for building up a protein called merlin, which is produced by schwann cells that surround nerve cells in the brain and spinal cord in the nervous system.

A previous study of the present inventor reported association between NF2 and RKIP in NF2 syndrome, the loss of NF2 reduces TβR2 expression and causes an imbalance between TβR1 and TβR2, and increased TβR1 phosphorylates RKIP and promotes RKIP instability.

Although TEW7197, a representative TGF-β inhibitor, inhibited schwannoma in a mouse model with NF2 syndrome by inhibiting an activity of TβR1 kinase (Mol Cancer Ther 17, 2271-2284, 2018), considering the physiological-pathological features of NF2 syndrome of which average onset occurs during adolescence or earlier and which is classified as a pediatric genetic disease, inhibition of TGF-β by TEW7197 may cause adverse effects because standard TGF-β is important for normal homeostasis and development.

Therefore, in order to develop a therapeutic agent for NF2 syndrome without side effects, it is very crucial to discover a novel candidate for NF2 syndrome that inhibits TβR1-mediated RKIP reduction without interfering with normal TGF-β signaling.

DISCLOSURE OF THE INVENTION

Technical Goals

An object of the present disclosure is to provide a pharmaceutical composition for preventing or treating neurofibromatosis type 2 (NF2) syndrome.

The other object of the present disclosure is to provide a health food composition for preventing or treating neurofibromatosis type 2 (NF2) syndrome.

Another object of the present disclosure is to provide a method of treating neurofibromatosis type 2 (NF2) syndrome.

Technical Solutions

In order to achieve the above object, the present disclosure provides a compound selected from a compound represented by the following Chemical Formula 1, a pharmaceutically acceptable salt thereof, a solvate thereof, or a stereoisomer thereof:

[Chemical Formula 1]

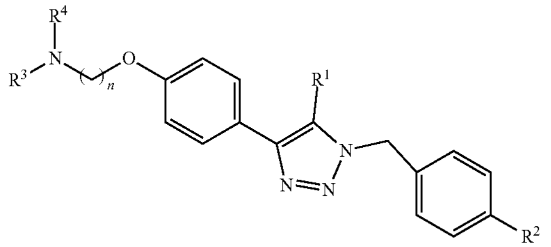

in the Chemical Formula 1, $R^1$ is $NR^5R^6$ or CN, $R^5$ or $R^6$ may be the same or different respectively and hydrogen or (C1~C4)alkyl, $R^2$ is halo, (C1~C4) alkyl, or (C1~C4)alkoxy, $R^3$ or R may be the same or different respectively and hydrogen, (C1~C4)alkyl, or (C1~C4) alkoxy, and n is an integer of 0 to 3.

In addition, the present disclosure provides a pharmaceutical composition for preventing or treating neurofibromatosis type 2 (NF2) syndrome or a health food composition for preventing or ameliorating neurofibromatosis type 2 syndrome, including the compound selected from the compound represented by Chemical Formula 1, a pharmaceutically acceptable salt thereof, a solvate thereof, or a stereoisomer thereof.

In addition, the present disclosure provides a method of treating neurofibromatosis type 2 (NF2) syndrome, including administering the compound represented by Chemical Formula 1, a pharmaceutically acceptable salt thereof, a solvate thereof, a stereoisomer thereof, or a combination thereof.

Advantageous Effects

A compound represented by Chemical Formula 1, a pharmaceutically acceptable salt thereof, a solvate thereof, a stereoisomer thereof, or a combination thereof according to the present disclosure inhibits, unlike TEW7197, a conventional TβR1 kinase inhibitor, TGF-β receptor 1 (TβR1)-mediated RKIP reduction without interfering with normal TGF-β signaling, and thus may be applied as a new type of therapeutic agent for neurofibromatosis type 2 syndrome to solve a problem concerning side effects caused by inhibition of normal TGF-β signaling.

BRIEF DESCRIPTION OF DRAWINGS

FIG. 1 shows results of screening RKIP inducers in NF2 cells, wherein (A) shows a result of Western blotting analysis on RKIP expression after carrying out a reaction with compounds (10 μM) in HEI-193 cells for 24 hours, and (B) shows a result of measuring cell viability via MTT assay after carrying out a reaction with compounds (10 μM) in HEI-193 cells or mouse schwannoma cells for 48 hours.

FIG. 2 shows results of identifying that 14 compounds (red marking) induce RKIP expression by reacting each compound (10 μM) in NF2 cells for 72 hours.

FIG. 3 shows a result of measuring cell viability via MTT assay by reacting each compound (10 μM) in normal fibroblasts for 48 hours.

FIG. 4 shows results of measuring cell viability via MTT assay after treating 39 derivatives related to Nf-08001 in HEI-193 cells (A), mouse schwannoma cells (B) or normal fibroblasts (C) for 48 hours respectively (TβPR1 inhibitors—TEW7197, SB431542, LY2157299; mTOR inhibitors—Rad001).

FIG. 5 shows results of compound derivation through optimization of NF-08001, wherein (A) shows results of measuring cell viability via MTT assay after treating an indicated concentration of compounds in HEI-193 cells or normal fibroblasts for 7 days, (B) shows a result of Western blotting analysis after co-culturing bead-conjugated GST RKIP recombinant proteins with TβR1-transfected HEK293 cell lysates and indicated compounds for 2 hours (+: 5 μM, ++: 10 M, SUP: Supernatant), (C) shows a result of reacting compounds at each concentration in HEI-193 cells for 24 hours, (D) shows a result of Western blotting analysis by treating 10 μM compounds in HEI-193 cells and then adding TGF-β1 (2 ng/ml) after 12 hours to carry out a reaction for 12 hours, and (E) shows a result of examining a 3TP-luciferase activity by transfecting HEK293 cells with 3TP-luciferase vectors, treating 10 μM compounds after 24 hours, and then adding TGF-β1 (2 ng/ml) after 12 hours to carry out a reaction.

FIG. 6 shows the other results related to compound derivation through optimization of NF-08001, wherein (A) shows results of reacting predetermined compounds in HEI-193 cells for 24 hours, (B) shows a result of Western blotting analysis after co-culturing bead-conjugated GST RKIP recombinant proteins with TβR1-transinfected HEK293 cell lysates and indicated compounds for 2 hours (SUP: Supernatant), and (C) shows a result of immunoblotting by treating 10 M compounds in normal fibroblasts for 24 hours.

FIG. 7 shows results of determining that the optimized Nf-08001 does not interfere with other signal pathways, wherein (A) shows a result of immunoblotting after reacting 10 μM compounds in HEI-193 cells, adding IGF-1 (5 μg/ml) after 12 hours, and culturing cells for 12 hours, and (B) shows a molecular structure of PRG-N-01.

FIG. 8 shows a selective effect of PRG-N-01 in NF2-deficient conditions, wherein (A) shows a result of performing IP analysis and Western blotting analysis by transfecting HEI-193 cells with FLAG-tagged TβR1 expression vectors, treating an indicated concentration of compounds after 24 hours, and eluting cells after 6 hours, (B) shows a result of measuring cell viability via MTT assay after transfecting HEI-193 cells with FLAG-tagged NF2 expression vectors, and after 24 hours, treating a predetermined concentration of compounds for 48 hours, (C) shows a result of performing immunoblotting after transfecting HEI-193 cells with FLAG-tagged NF2 expression vectors, and after 24 hours, treating indicated compounds (10 μM) for 24 hours, (D) shows a result of examining a 3TP-luciferase activity by transfecting HEI-193 cells with 3TP-luciferase vectors by treating indicated compounds after 24 hours, and adding TGF-β1 (2 ng/ml) after 12 hours to carry out a reaction for 12 hours (TβR1 inhibitor-TEW7197, LY2157299), and (E) shows a result of performing immunoblotting after transfecting HEI-193 cells and mouse schwannoma cells with predetermined expression vectors (WT: Wild type, TA: T101A mutant, TD: T101D mutant), and 24 hours later, treating indicated compounds (10 M) for 24 hours.

FIG. 9 shows results of examining effects of PRG-N-01, wherein (A) shows a result of performing IP analysis and Western blotting analysis by transfecting HEI-193 cells with HA-tagged RKIP expression vectors, treating an indicated concentration of compounds after 24 hours, and eluting cells after 6 hours, (B) shows a result of immunoblotting after treating cells with PRG-N-01 or TEW7197 for 36 hours, (C) shows a result of performing immunoblotting by transfecting mouse schwannoma cells with FLAG-tagged NF2 expression vectors, and after 24 hours, treating predetermined compounds (10 μM) for 24 hours, (D) shows a result of measuring cell viability via MTT analysis after transfecting mouse schwannoma cells with FLAG-tagged NF2 expression vectors and treating a predetermined concentration of compounds for 48 hours, and (E) shows a result of performing immunoblotting by transfecting HEI-193 cells with indicated expression vectors (WT: Wild type, RKIP T101A: Mutant), and after 24 hours, treating predetermined compounds (2 μM) for 48 hours for further reaction with TGF-β1 (2 ng/ml) for 12 hours.

FIG. 10 shows results of gene expression profile in NF2 cells treated with PRG-N-01, wherein (A) shows a result of microarray after treating an indicated concentration of PRG-N-01 in HEI-193 cells for an indicated time, wherein Cluster A is an upregulated gene set, and Cluster B is a downregulated gene set, and (B-C) show results of GO term analysis of genes expressed differently in a control group and 2 μM PRG-N-01-treated HEI-193 cells (Red bar: Lipid metabolism-related processes; Blue bar: Cell cycle arrest-related processes), and (D) shows a table in which representative genes related to lipid metabolism or cell cycle are listed.

FIG. 11 shows the other results of the gene expression profile in PRG-N-01-treated NF2 cells, wherein (A-B) show results of cell components (CCs) or a molecular function (MF) in GO term analysis of genes expressed differently in a control group and HEI-193 cells treated with 2 M PRG-N-01 for 6 days, and (C-F) show results of GO term analysis of genes expressed differently in the control group and HEI-193 cells treated with 1 μM PRG-N-01 for 6 days.

FIG. 12 shows results that PRG-N-01 inhibits a cell-cycle and promotes differentiation into schwann cells, wherein (A) shows a result of performing cell cycle analysis by treating 10 μM PRG-N-01 in HEI-193 cells for 4 days, (B) shows a result of treating 10 μM PRG-N-01 in HEI-193 cells for an indicated time and counting the cells, (C) shows a result of treating PRG-N-01 in HEI-193 cells for 7 days or transfecting with FLAG-tagged NF2 expression vectors to induce differentiation, (D-E) show results of applying HEI-193 cells reacted with predetermined compounds to RT-PCR (D) or Western blotting analysis (E) (TEW: TEW7197; SB: SB431542), and (F-G) show results of performing FACS assay (F) or immunofluorescence analysis (G) by staining HEI-193 cells with anti-schwann cell marker protein antibody.

FIG. 13 shows the other results that PRG-N-01 inhibits a cell-cycle and promotes differentiation into schwann cells, wherein (A) shows a result of performing cell-cycle analysis by treating 10 M PRG-N-01 in HEI-193 cells for 4 days, (B) shows a result of treating 10 μM PRG-N-01 in HEI-193 cells for 7 days, fixing the cells with 4% paraformaldehyde, and staining with paloidine to induce differentiation, (C) shows a result of identifying schwann cell markers (MPZ and PMP22) by treating PRG-N-01 at indicated concentrations in HEI-193 cells for 7 days, and (D) shows a result of treating 10 M PRG-N-01 in HEI-193 cells for 7 days and staining with anti-schwann cell marker protein antibody.

FIG. 14 shows results that PRG-N-01 induces expression of RKIP to inhibit stemness of schwannoma, wherein (A) shows a result of performing Western blotting after treating a predetermined concentration of PRG-N-01 or TEW7197 in HEI-193 cells for 4 days, (B) shows an image of tumorspheres captured on the $10^{th}$ day after reacting HEI-193 cells or schwannoma cells with predetermined compounds (10 μM) in DMEM/F12 medium, (C-D) show results of reacting HEI-193 cells or schwannoma cells with predetermined compounds (10 μM) in DMEM/F12 medium, lysing tumorspheres on the $10^{th}$ day, and performing immunoblotting using indicated antibody, (E) shows a result of Western blotting analysis of tumorspheres, (F) shows a result of immunoblotting by treating HEI-193 cells with leptomycin B (2 ng/ml) for inhibition of nuclear export, adding, after 6 hours, 10 μM predetermined compounds, and performing culture for 24 hours, and (G) shows a result of immunoblotting by treating HEI-193 cells with MG132 (5 μM) for inhibition of proteasome degradation, adding, after 6 hours, 10 μM indicated compounds, and performing culture for 24 hours.

FIG. 15 shows the other results that PRG-N-01 induces RKIP to inhibit stemness of schwannoma, wherein (A) shows an image of tumorspheres captured on the $4^{th}$ day after treating HEI-193 cells with indicated compounds (10 μM) in DMEM/F12 medium for indicated days, (B) shows a result of treating HEI-193 cells with indicated compounds (10 μM) in DMEM/F12 medium, lysing tumorspheres on the $10^{th}$ day, and performing immunoblotting using indicated antibody, (C) shows a result of treating indicated compounds (2 M) in HEI-193 cells for 24 hours and staining with anti-SOX2 antibody, (D) shows a result of performing Western blotting after treating indicated compounds (2 μM) in HEI-193 cells for 24 hours and performing cell fractionation, (E) shows a result of immunoblotting after transfecting HEI-193 cells with indicated expression vectors (WT: Wild type, TA: RKIP T101A mutant, TD: RKIP T101D mutant), and after 24 hours, treating indicated compounds (10 μM) for 24 hours, and (F) shows a result of immunoblotting after transfecting HEI-193 cells with indicated siRNA, and after 24 hours, treating indicated compounds (2 μM) for 24 hours.

FIG. 16 shows results revealing that RKIP is a critical factor in SOX2 reduction and TGF-β signaling in schwannoma cells, wherein (A) shows a result of performing immunoblotting by treating 10 μM PRG-N-01 in HEI-193 cells, adding TGF-β1 (1 ng/ml) after 12 hours, and carrying out a reaction for an indicated time, (B) shows a result of fixing HEI-193 cells with 4% paraformaldehyde and staining with anti-phospho-SMAD2/3 antibody, and (C-D) show results of performing immunoblotting by transfecting HEI-193 cells with indicated expression vectors, adding indicated concentration of TGF-β1 after 12 hours, and carrying out a reaction for an indicated time.

FIG. 17 shows in vivo antitumor effects of PRG-N-01, wherein (A) shows a tumor image at 5 weeks of administration by administering a carrier or PRG-N-01 (20 mg/kg) to mice when a tumor volume reached 300 $mm^3$ for 5 weeks (3 times a week), (B) shows a quantified weight of a tumor separated by incising mice after 5 weeks of administration, (C) shows a volume of tumor measured every week, and (D-E) show results of performing immunoblotting and RT-PCR by extracting proteins and mRNA from isolated tumors.

FIG. 18 shows the other in vivo antitumor effects of PRG-N-01, wherein (A) shows images of tumor-transplanted mice at 5 weeks of PRG-N-01 administration, and (B) shows a weight of mice measured after intraperitoneally administrating a high concentration of PRG-N-01 (200 mg/kg) to examine toxicity of PRG-N-01.

BEST MODE FOR CARRYING OUT THE INVENTION

Hereinafter, the present disclosure will be described in more detail.

As a result of endeavor to discover a novel candidate for treatment of NF2 syndrome that inhibits TβR1-mediated RKIP reduction without interfering with normal TGF-β signaling, the present inventor completed the present disclosure by determining that PRG-N-01, a novel compound, promotes differentiation of cells involved in NF2 syndrome and inhibits tumor growth in allograft tumor models without interference with normal TGF-β signaling.

The present disclosure provides a compound selected from a compound represented by the following Chemical Formula 1, a pharmaceutically acceptable salt thereof, a solvate thereof, or a stereoisomer thereof:

[Chemical Formula 1]

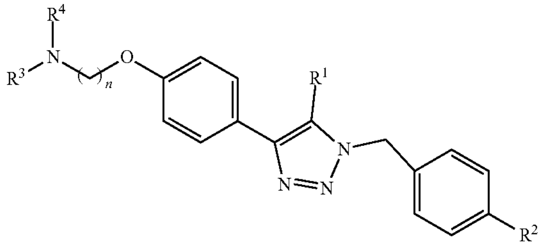

in the Chemical Formula 1, $R^1$ is $NR^5R^6$ or CN, $R^5$ or $R^6$ may be the same or different respectively and hydrogen or (C1~C4)alkyl, $R^2$ is halo, (C1~C4)alkyl, or (C1~C4)alkoxy, $R^3$ or $R^4$ may be the same or different respectively and hydrogen, (C1~C4) alkyl, or (C1~C4)alkoxy, and n is an integer of 0 to 3.

Preferably, in the compound represented by Chemical Formula 1, $R^1$ is $NH_2$ or $NR^5R^6$, $R^5$ or $R^6$ may be the same or different respectively and (C1~C2)alkyl, $R^2$ is (C1~C4) alkoxy, $R^3$ or $R^4$ may be the same or different respectively and (C1~C4)alkyl, and n may be an integer of 1 to 2.

More preferably, in the compound represented by Chemical Formula 1, $R^1$ is $NH_2$, $R^2$ is (C1~C2)alkoxy, $R^3$ and $R^4$ are (C1~C2)alkyl, and n may be an integer of 1 to 2.

More preferably, the compound may be a compound (PRG-N-01) represented by the following Chemical Formula 2.

[Chemical Formula 2]

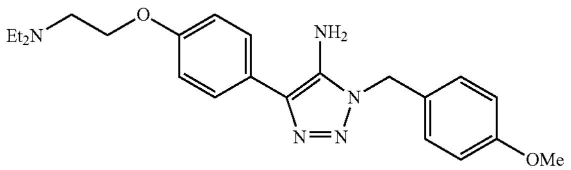

PRG-N-01

The present disclosure provides a pharmaceutical composition for preventing or treating neurofibromatosis type 2 (NF2) syndrome, including a compound selected from the compound represented by Chemical Formula 1, a pharmaceutically acceptable salt thereof, a solvate thereof, or a stereoisomer thereof.

The compound according to the present disclosure may inhibit an interaction between TGF-β receptor 1 (TβR1) and RKIP and particularly inhibit TGF-β receptor 1 (TβR1)-mediated RKIP reduction without interfering with normal TGF-β signaling.

In addition, the compound according to the present disclosure may suppress a cell cycle to promote differentiation into schwann cells and induce RKIP to inhibit sternness of schwannoma cells.

In the present disclosure, the pharmaceutically acceptable salt may be one or more basic salts selected from the group consisting of sodium salts, potassium salts, calcium salts, lithium salts, magnesium salts, cesium salts, aminium salts, ammonium salts, triethyl aminium salts, and pyridinium salts, but is not limited thereto.

In addition, the pharmaceutically acceptable salts may be one or more acidic salts selected from the group consisting of hydrochloric acid, bromic acid, sulfuric acid, sulfurous acid, sulfurous acid, phosphoric acid, citric acid, acetic acid, maleic acid, fumaric acid, gluconic acid, methanesulfonic acid, benzenesulfonic acid, campersulfonic acid, oxalic acid, malonic acid, glutaric acid, acetic acid, glycolic acid, succinic acid, tartaric acid, 4-toluene sulfonic acid, galacturonic acid, embonic acid, glutamic acid, citric acid, and aspartic acid, but are not limited thereto.

The pharmaceutical composition of the present disclosure may include a pharmaceutically acceptable carrier, excipient, or diluent in addition to the above-described components for administration. The carrier, excipient and diluent may include lactose, dextrose, sucrose, sorbitol, mannitol, xylitol, erythritol, maltitol, starch, gum acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, and mineral oil.

The pharmaceutical composition of the present disclosure may be used by being formulated in the form of oral formulations such as acids, granules, tablets, capsules, suspensions, emulsions, syrups, and aerosols, topical agents, suppositories, or sterile injection solutions according to the conventional methods, respectively. Specifically, when formulated, it may be prepared using a diluent or excipient such as fillers, weight agents, binding agents, humectants, disintegrants, and surfactants that are used conventionally. Solid preparations for oral administration include tablets, pills, acids, granules, and capsules, but are not limited thereto. Such solid preparations may be prepared by mixing at least one or more excipients such as starch, calcium carbonate, sucrose, lactose, and gelatin, in addition to the above active ingredients. In addition to simple excipients, lubricants such as magnesium stearate and talc may also be used. In addition to liquid substances and liquid paraffin for oral use, various excipients, such as wetting agents, sweeteners, aromatics, and preservatives may be added for preparation. Preparations for parenteral administration include sterilized aqueous solutions, non-aqueous solvents, suspensions, emulsions, lyophilized preparations, and suppositories. As non-aqueous solvents and suspensions, propylene glycol, polyethylene glycol, vegetable oils such as olive oil, injectable ester such as ethyl oleate may be used. As a base of suppositories, Witepsol, Macrogol, Tween 61, cacao butter, laurin fat, and glycerogelatin may be used.

The pharmaceutical composition of the present disclosure may be prepared as oral or parenteral preparations and administered orally, intravenously, intraventricularly, intradermally, intramuscularly, intraperitoneal, nasal, or epidural routes, but are not limited thereto.

Suitable dosage of the pharmaceutical composition of the present disclosure may vary depending on the condition and weight of a patient, severity of a disease, drug form, and time, but may be appropriately selected by those skilled in the art, such that the daily dosage of the composition may preferably be 0.01 mg/kg to 100 mg/kg and administration may be performed in single to several divided doses a day as needed.

In addition, the present disclosure provides a health food composition for preventing or ameliorating neurofibromatosis type 2 syndrome, including a compound selected from the compound represented by Chemical Formula 1, a pharmaceutically acceptable salt thereof, a solvate thereof, or a stereoisomer thereof.

The health food composition may include various nutritional supplements, vitamins, minerals (electrolytes), flavoring agents such as synthetic flavoring agents and natural flavoring agents, colorants and thickeners (cheese, chocolate, etc.), pectic acid and salts thereof, alginic acid and salts thereof, organic acids, protective colloidal thickeners, pH regulators, stabilizers, preservatives, glycerin, alcohol, and carbonating agents that are used in carbonated beverages. Additionally, it may also include pulp for manufacture of natural fruit juices, synthetic fruit juices, and vegetable beverages. These components may be used independently or in combination. In addition, the health functional food composition may be in any one form of meat, sausage, bread, chocolate, candy, snacks, confectionery, pizza, ramen, chewing gum, ice cream, soup, beverage, tea, functional water, drink, alcohol, and vitamin complex.

The health functional food composition may additionally include food additives, and the suitability as the food additive is determined by the standards and criteria related to corresponding items according to the general rules and general test methods of Korean Food Additives Codex approved by the Ministry of Food and Drug Safety, unless otherwise stipulated.

The items listed in the Korean Food Additives Codex may include, for example, chemically synthesized compounds such as ketones, glycine, potassium citrate, nicotinic acid, and cinnamic acid, natural additives such as persimmon color, licorice extracts, crystallized cellulose, kaoliang color, and guar gum, and mixed preparations such as sodium L-glutamate preparations, noodle-added alkali agents, preservative agents, and tar color agents.

In this case, the content of the composition according to the present disclosure added to food in the process of preparing health food compositions may be appropriately adjusted as needed.

In addition, the present disclosure provides a method of treating neurofibromatosis type 2 (NF2) syndrome, including administering the compound represented by Chemical Formula 1, a pharmaceutically acceptable salt thereof, a solvate thereof, a stereoisomer thereof, or a combination thereof.

MODES FOR CARRYING OUT THE INVENTION

Hereinafter, the present disclosure will be described in more detail through example embodiments and experimental examples. These example embodiments and experimental examples are only for the purpose of describing the present disclosure in more detail, and it will be apparent to those skilled in the art that the scope of the present disclosure is not limited by these example embodiments and experimental examples according to the gist of the present disclosure.

[Scheme 1]

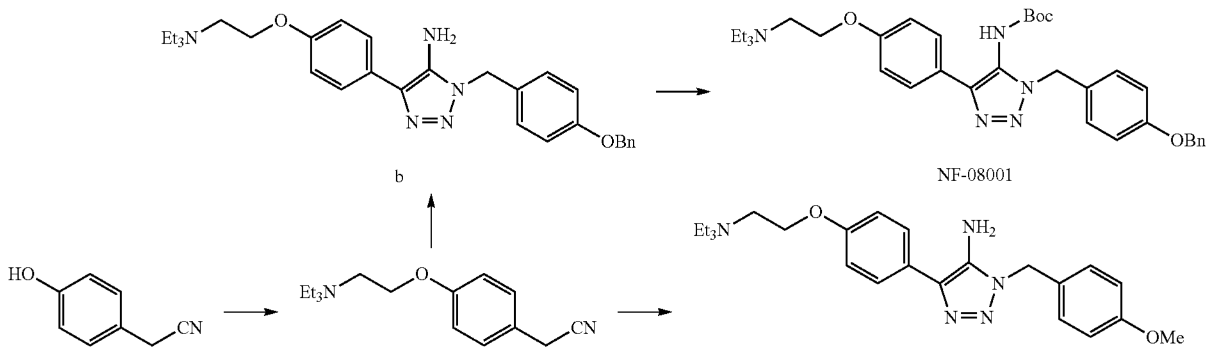

b

NF-08001 a

NF-18001

Synthesis Example 1: Synthesis of NF-08001

1. Synthesis of 2-(4-(2-(diethylamino)ethoxy)phenyl)acetonitrile (a)

Diisopropyl azodicarboxylate (1.5 equivalent) and 2-(diethylamino)ethan-1-ol (1.3 equivalent; 300 mg, 2.25 mmol) were added, under argon atmosphere at 0° C., to a solution in which 2-(4-hydroxyphenyl)acetonitrile (1 equivalent) and $PPh_3$ (1.3 equivalent) were mixed in THF. After stirring at room temperature for 3 hours, a reaction was stopped with water, followed by extraction using EtOAc. An organic phase obtained by extraction was dried with $MgSO_4$ and concentrated in vacuum. The residue was purified by silica gel-based flash column chromatography (MeOH:EtOAc=1:9) to obtain a yellow oil compound a [530 mg (99%)].

2. Synthesis of 1-(4-(benzyloxy)benzyl)-4-(4-(2-(diethylamino)ethoxy)phenyl)-1H-1,2,3-triazol-5-amine (b)

t-BuOK (0.25 equivalent; 1.0 M dissolved in THF) was added, under argon atmosphere at room temperature, to a solution in which 2-(4-(2-(diethylamino)ethoxy)phenyl)acetonitrile (a) [1 equivalent; 118 mg, 0.51 mmol] and 1-(azidomethyl)-4-(benzyloxy)benzene [1 equivalent; 98.8 mg, 0.41 mmol] were mixed in DMSO. After stirring at the same temperature for 6 hours, a reaction was stopped with $NH_4Cl$, followed by extraction with EtOAc. The organic phase obtained by extraction was dried using $MgSO_4$ and concentrated in vacuum. The residue was purified by silica gel-based flash column chromatography ($MeOH:CH_2Cl_2$=1:10) to obtain an ivory-colored solid compound b [1.12 g (70%)].

$^1H$ NMR ($CDCl_3$, 400 MHz) δ 7.54 (d, 2H, J=8.6 Hz), 7.38 (m, 4H), 7.32 (t, 1H, J=6.4 Hz), 7.20 (d, 2H J=8.5 Hz), 6.95 (m, 4H), 5.36 (s, 2H), 5.03 (s, 2H), 4.10 (t, 2H, J=6.1 Hz), 3.64 (s, 2H), 2.93 (t, 2H, J=6.1 Hz), 2.70 (q, 4H, J=7.2 Hz), 1.10 (t, 6H, 7.1 Hz);

$^{13}C$ NMR ($CDCl_3$, 100 MHz) δ 159.0, 157.9, 136.8, 136.7, 131.6, 128.9, 128.7, 128.2, 127.6, 127.2, 126.6, 124.4, 115.6, 115.1, 70.2, 66.2, 51.7, 50.4, 47.8, 11.6; HRMS ($ESI^+$) m/z: $[M+H]^+$ calcd for $C_{28}H_{34}N_5O_2$ 472.2707. found 472.2713.

3. Synthesis of tert-butyl(1-(4-(benzyloxy)benzyl)-4-(4-(2-diethylamino)ethoxy)phenyl)-1H-1,2,3-triazol-5-yl)carbamate [NF-08001]

TEA (73.0 μL, 0.52 mmol), $Boc_2O$ (60.2 μL, 0.26 mmol), and DMAP (3.0 mg, 0.026 mmol) were added, at room temperature, to a solution in which 1-(4-(benzyloxy)benzyl)-4-(4-(2-(diethylamino)ethoxy)phenyl)-1H-1,2,3-triazol-5-amine (b) was dissolved in $CH_2Cl_2$ (25 ml). After stirring at the same temperature for 3 days, a reaction was stopped with water, followed by extraction with $CH_2Cl_2$. The organic phase obtained by extraction was dried using $Na_2SO_4$ and concentrated in a vacuum. The residue was purified by silica gel-based flash column chromatography (MeOH:EtOAc=1:10) to obtain a compound [NF-08001] [15.0 mg (10%)].

$^1H$ NMR ($CDCl_3$, 500 MHz) δ 7.61 (d, 2H, J=8.8 Hz), 7.38 (m, 5H), 7.31 (m, 1H), 7.26 (d, 2H, J=8.6 Hz), 6.92 (m, 4H), 5.31 (s, 2H), 5.02 (s, 2H), 4.07 (t, 2H, J=6.2 Hz), 2.89 (t, 2H, J=6.2 Hz), 2.66 (q, 4H, J=7.1 Hz), 1.25 (s, 1H), 1.16 (s, 9H), 1.07 (t, 6H, J=7.1 Hz);

$^{13}C$ NMR ($CDCl_3$, 125 MHz) δ 159.1, 159.0, 148.7, 141.0, 136.7, 131.2, 129.8, 128.8, 128.2, 127.5, 127.1, 126.2, 122.6, 115.3, 115.0, 84.7, 70.1, 66.5, 51.6, 51.4, 47.9, 27.6, 11.7; HRMS ($ESI^+$) m/z: $[M+H]^+$ calcd for $C_{33}H_{42}N_5O_4$ 572.3231. found 572.3233.

Synthesis Example 2: Synthesis of PRG-N-01

Synthesis of 4-(4-(2-(diethylamino)ethoxy)phenyl)-1-(4-methoxybenzyl)-1H-1,2,3-triazol-5-amino [PRG-N-01]

t-BuOK (0.25 equivalent; 1.0 M dissolved in THF) was added, under argon atmosphere at room temperature, to a solution in which 2-(4-(2-diethylamino)ethoxy)phenyl)acetonitrile (a) [1 equivalent; 659 mg, 4.04 mmol] and 1-(azidomethyl)-4-methoxybenzene [1 equivalent; 864 mg, 3.72 mmol] were mixed in DMSO. After stirring at the same temperature for 6 hours, a reaction was stopped with $NH_4Cl$, followed by extraction using EtOAc. An organic phase obtained by extraction was dried with $MgSO_4$ and concentrated in vacuum. The residue was purified by silica gel-based flash column chromatography ($MeOH:CH_2Cl_2=1:10$) to obtain an ivory-colored solid compound [PRG-N-01] [1.12 g (70%)].

$^1H$ NMR ($CDCl_3$, 400 MHz) δ 7.53 (d, 2H, J=8.9 Hz), 7.19 (d, 2H, J=8.4 Hz), 6.94 (d, 2H, J=8.8 Hz), 6.87 (d, 2H, J=8.7 Hz), 5.36 (s, 2H), 4.07 (t, 2H, J=6.2 Hz), 3.77 (s, 3H), 3.64 (s, 2H), 2.89 (t, 2H, J=6.2 Hz), 2.66 (q, 4H, J=7.1 Hz), 1.07 (t, 6H, J=7.2 Hz);

$^{13}C$ NMR ($CDCl_3$, 100 MHz) δ 159.8, 158.0, 136.7, 131.6, 128.9, 127.2, 126.3, 124.3, 115.1, 114.7, 66.5, 55.4, 51.7, 50.4, 47.9, 11.8; HRMS ($ESI^+$) m/z: $[M+H]^+$ calcd for $C_{22}H_{30}N_5O_2$ 396.2394. found 396.2402.

Example 1: Preparation of Cell Lines and Mice

1. Preparation of Cell Lines

HEK293 cell lines were obtained from the American Type culture collection (ATCC, Manassas, VA). A human schwannoma cell line HEI-193 (NF2 deficient) was provided by Dr. Zadeh G (University Health Network, Toronto, Canada). Mouse schwann cells (Giovannini et al., 2000) derived from $NF2^{flox}$ mice were subjected to in vitro Cre-mediated deletion and then transduced with pMSCV-hygro retroviral rescue constructs encoded by any one of full-length merlin isoform 1 or an empty vector (named MSchw-WT and Mschw-KO, respectively). These cell lines were provided by Dr Greer P (Queen's University, Ontario, CANADA). Normal fibroblasts (GM00038, 9-year-old female N9) were obtained from Coriell Cell Repositories (Camden, NJ, USA) and cultured in Eagle's minimal essential medium (EMEM) supplemented with 15% fetal bovine serum (FBS) and 2 mM glutamine without antibiotics.

All cells were maintained in a 5% $CO_2$ humidification incubator at 37° C. HEI-193, HEK293, and mouse schwann cells were cultured in liquid DMEM medium supplemented with 10% FBS and 1% antibiotics. The appearance and growth characteristics of all cells used in this experiment were compared with published information to ensure their authenticity.

2. Preparation of Mice

All experimental procedures involving animal experiments were approved by the Animal Care Committee of Pusan National University. FVB/NJ mice were obtained from Jackson Laboratory. Before the experiment, all mice were maintained under temperature- and light-controlled conditions (20-23° C., 12 hours/12 hours of light/dark cycle) and provided with autoclaved food and water ad libitum.

Example 2: Preparation of Vectors and Transfection, siRNA, and Antibody

1. Vectors and Transfection pCMV RKIP-HA was provided by Keum G (David Geffen School of Medicine at University of California, Los Angeles, CA, USA). pCMV RKIP-T101A-HA and pCMV RKIP-T101D-HA were generated by Dr. J. H. Hwang (Pusan National University). pcDNA3 NF2-FLAG, pRK5 TGF beta type 1 receptor-FLAG, and TGF beta type 2 receptor-HA were obtained from Addgene (Cambridge, MA, USA). Transfection was performed using the Jetpei transfection agent (Polyplus New York, USA) for mammalian expression of these vectors.

In other words, cells were seeded at a density of $2\times10^5$ cells/well in 12-well plates and cultured overnight before transfection. The vector (1.5 μg) was mixed with 1.5 μl of Jetpei reagent dissolved in 150 mM NaCl solution. The mixture was reacted at room temperature for 15 minutes, and then added to the cells. After 3 hours, the serum-free medium was replaced with medium supplemented with 10% FBS.

2. Preparation of siRNA

For in vitro gene knock down, siRNAs against target proteins were generated (Cosmo Genetech, Seoul, Korea). The sequence of si-RKIP was [CACCAGCATTTCGTGG-GATGGTCTTTCAAGAGAAGACCATCC-CACGAAATGCTG GTG (SEQ ID NO: 1)]. INTERFERin transfection reagent (Polyplus New York, USA) was used for transfection of siRNA. Briefly, cells were seeded at a density of 2×105 cells/well on 12-well plates and cultured overnight before transfection. A total of 1.5 pmole of siRNA (21 ng) duplexes were mixed with 4 μl of INTERFERin transfection reagent in 100 μl of medium without serum. The mixture was reacted at room temperature for 15 minutes to allow formation of the INTERFERin/siRNA complex. These complexes were added to the cells and reacted for another 4 hours, after which the serum-free medium was replaced with medium supplemented with 10% FBS.

3. Antibody

Antibodies against RKIP (1: 2000 for immunoblotting, ab76582), SOX10 (1:1000 for immunoblotting and 1:200 for immunofluorescence, ab155279), myelin PLP (1:500 for immunoblotting and 1:300 for immunofluorescence, ab155279), MBP (1:500 for immunoblotting, 1:300 for immunofluorescence, 1:200 for FACS, ab62631), MPZ (1:500 for immunoblotting, ab31851), GFAP (1:100 for FACS, 1:300 for immunofluorescence, ab270270), TβR1 (1:500 for immunoblotting, ab31013), and tenascin C (1:1000 for immunoblotting, ac108930) were purchased from Abcam, respectively.

SOX2 (1:1000 for immunoblotting and 1:300 for immunofluorescence, 3579), Oct-4A (1:1000 for immunoblotting, 2840), NANOG (1:1000 for immunoblotting, 4903), c-Myc (1:1000 for immunoblotting, 5605), p-SMAD2/3 (1:1000 for immunoblotting, 8828), Erk (1:1000 for immunoblotting, 9102), p-Erk (1:1000 for immunoblotting, 9101), p-AKT S473 (1:1000 for immunoblotting, 9271), and GFAP (1:500 for immunoblotting and 1:300 immunofluorescence, 3670) were purchased from Cell Signaling Technology. Antibodies against anti-β-actin (1:3000 for immunoblotting, 66009-1-Ig) and HA (1:1000 for immunoblotting, 51064-2-AP) were purchased from Proteintech, respectively.

Anti-FLAG (1:2000, F1804) antibody was purchased from Sigma, antibody specific for GST (1:1000 for immunoblotting, sc-138) was purchased from Santa Cruz Biotechnology, and anti-TβR2 (1: 500 for immunoblotting, bs-0117R) antibody was purchased from Bioss.

4. Preparation of Reagents

Silica (S5631, silicon dioxide) and TβR1 kinase inhibitors (SB431542 and LY2157299) were purchased from Sigma Aldrich (St, Louis, Mo, USA). Procrine TGF-γ1 was purchased from R&D systems (Minneapolis, MN, USA). N-((4-([1,2,4]triazolo[1,5-a]pyridin-6-yl)-5-(6-methylpyridin-2-yl)-1H-imidazol-2-yl)methyl)-2-fluoroaniline (TEW7197) was provided by Dr. Sung Soo Kim (CHA University, Sungnam, Seoul, Korea). The TEW7197 was synthesized based on a previous paper (Med Chem. 2014 May 22; 57(10):4213-38).

[Structure of TEW7197]

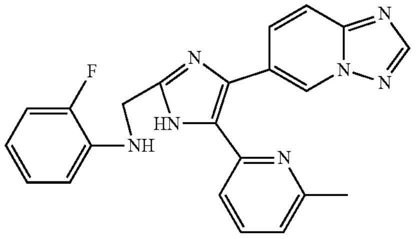 [SMILES: Cc1cccc(-c2[nH]c(CNc3ccccc3F)nc2-c2ccc3ncnn3c2)n1]

Example 3: RT-PCR Analysis

For RT-PCR, total cellular RNA was extracted using an RNA extraction kit (Qiagen). Gene expression analysis was performed using cDNA synthesized from total RNA with MMLV RT (Invitrogen, Carlsbad, USA) and random hexamer. PCR from genomic DNA was performed using Dia-Star Taq DNA polymerase (SolGent, Daejeon, Korea), and gene expression analysis was performed using the following specific primers:

hSOX2 (Forward)
(SEQ ID NO: 2)
5'-TCGCAGACCTACATGAACGG-3' hSOX2 (Reverse)
(SEQ ID NO: 2)
5'-ACATGTGAAGTCTGCTGGGG-3' hSOX10 (Forward)
(SEQ ID NO: 4)
5'-CATGGAGACCTTTGATGTGGC-3' hSOX10 (Reverse)
(SEQ ID NO: 5)
5'-TCAGAGTAGTCAAACTGGGGG-3' hMBP (Forward)
(SEQ ID NO: 6)
5'-CAAGTACCATGGACCATGCC-3' hMBP (Reverse)
(SEQ ID NO: 7)
5'-TTTATAGTCGGACGCTCTGCC-3' hMPZ (Forward)
(SEQ ID NO: 8)
5'-CAACCCTACATTGACGAGGTG-3' hMPZ (Reverse)
(SEQ ID NO: 9)
5'-CACTGACAGCTTTGGTGCTTC-3'

-continued hPMP22 (Forward)
(SEQ ID NO: 10)
5'-GCAATGGACACGCAACTGATC-3' hPMP22 (Reverse)
(SEQ ID NO: 11)
5'-CGAAACCGTAGGAGTAATCCG-3' mSOX2 (Forward)
(SEQ ID NO: 12)
5'-AGGATAAGTACACGCTTCCCG-3' mSOX2 (Reverse)
(SEQ ID NO: 13)
5'-TAGGACATGCTGTAGGTGGG-3' mSOX10 (Forward)
(SEQ ID NO: 14)
5'-ACTACAAGTACCAACCTCGGC-3' mSOX10 (Reverse)
(SEQ ID NO: 15)
5'-GTTGGACATTACCTCGTGGC-3' mMBP (Forward)
(SEQ ID NO: 16)
5-'TTCTTTAGCGGTGACAGGGG-3' mMBP (Reverse)
(SEQ ID NO: 17)
5'-TAAATCTGCTGAGGGACAGGC-3' mMPZ (Forward)
(SEQ ID NO: 18)
5-'CTGCTCCTTCTGGTCCAGTGAA-3' mMPZ (Reverse)
(SEQ ID NO: 19)
5'-AGGTTGTCCCTTGGCATAGTGG-3' mPMP22 (Forward)
(SEQ ID NO: 20)
5'-CGTCCAACACTGCTACTCCTCA-3' mPMP22 (Reverse)
(SEQ ID NO: 21)
5'-GCCTTTGGTGAGAGTGAAGAGC-3'

Example 4: Analysis of Protein-Protein Interaction

For protein-protein interaction analysis, glutathione S-transferase (GST)-pull down assay was performed. For GST-pull down, agarose-bead-conjugated GST-RKIP recombinant protein was reacted with FLAG-tagged TβR1-transfected HEK 293 cell lysates in PBS buffer at 4° C. for 1 hour. Immunoprecipitation (IP) assay was performed by reacting with FLAG-tagged TβR1- or HA-tagged RKIP-transfected HEI-193 cell lysates in PBS buffer. Whole lysates were reacted with appropriate primary antibodies at 4° C. for 2 hours and with agarose-bead-conjugated protein A/G (Invitrogen, Carlsbad, CA, USA) for 2 hours. After centrifugation, the precipitates were washed twice with RIPA buffer and subjected to SDS-PAGE and western blotting analysis.

Example 5: Western Blotting Analysis

Cells were harvested and lysed using RIPA buffer [50 mM Tris-Cl, pH 7.5, 150 mM NaCl, 1% NP-40, 0.1% SDS, and 10% sodium deoxycholate] to examine cellular signaling. Protein concentrations in samples were measured using Bio-Rad (Hercules, CA, USA) protein assay kits and BSA standards. The samples (20 μg protein per lane) were separated by sodium dodecyl sulfate-polyacrylamide gel electrophoresis (SDS-PAGE), transferred to Immobilon-$P^{SQ}$ transfer membranes (Millipore Corp., MA, USA), which were then cultured with 3% skim milk-containing TBS-T buffer (Tris-HCl-based buffer containing 20 mM Tris pH 7.6, 150 mM NaCl, and 0.05% Tween 20) for 1 hour at room temperature and then reacted with primary antibody in TBS-T overnight at 4° C. The membranes were then washed and reacted with secondary horseradish peroxidase (HRP)-conjugated antibodies [goat anti-mouse, goat anti-rabbit, and mouse anti-goat antibodies (Pierce, Thermo Fisher Scientific, Inc., Rockford, IL, USA)] in TBS-T at room temperature for 2 hours. The blots were detected using an HRP-conjugated secondary antibody using ECL kit (Intron, Seoul, Korea).

Example 6: Immunofluorescence Staining

Cells were seeded on cover glass, washed with PBS, fixed with 4% paraformaldehyde (PFA) for 30 minutes at room temperature, and then permeabilized with 0.2% Triton X-100 at room temperature for 5 minutes. After treatment with blocking buffer [3% goat serum diluted in PBS] for 1 hour, cells were reacted with the specified antibody in the blocking buffer overnight at 4° C. Finally, the cells were reacted with secondary antibodies conjugated with FITC or rhodamine at 4° C. for 7 hours. The nuclei were stained with DAPI at room temperature for 10 minutes. After the cells were washed 3 times with PBS, the cover glass was mounted with a mounting solution (H-5501, Vector Laboratories, Cambridgeshire, UK) and immunofluorescence signals were detected using a fluorescence microscopy (Zeiss, Jena, Germany).

Example 7: MTT Assay

To measure cell viability, MTT (3-(4,5-dimethylthiazol-2-yl)-2,5-diphenyltetrazolium bromide) assay was used. In other words, the cells were seeded in 96-well plates and treated with the indicated chemicals for a predetermined time. After removing the medium, 200 µl of MTT solution (0.5 mg/ml) dissolved in PBS was added to each well. Plates were then cultured at 37° C. for 4 hours, the MTT solution was removed, the precipitated substances were dissolved using a solution (DMSO:ethanol=1:1), and an amount of formazan dye produced was quantified by measuring the absorbance at 560 nm using an ELISA microplate reader (Thermo Fisher Scientific, MA, USA).

Example 8: Allograft Tumor Growth Assay, Tumorsphere Formation Assay, and Flow Cytometry For allograft, $1\times10^7$ mouse schwannoma cells were seeded subcutaneously on FVB/NJ mice (8 weeks old). Tumor-bearing mice were administered with the carrier (n=8) or PRG-N-01 (20 mg/kg; n=8) by intraperitoneal injection for 5 weeks (3 times per week). Every week, the tumor volume and body weight were measured. After termination of the experiment in each group, mice were dissected, and tumor tissues were isolated.

For tumorsphere formation assay, Hei-193 or mouse schwannoma cells ($3\times10^6$ cells/plate) were cultured in DMEM/F12 medium (supplemented with 2% B27 and 40 ng/ml bFGF) and added with the indicated chemicals on non-coated plates for indicated days.

In addition, for flow cytometry, cells were seeded in a 6-well plate and reacted with DMSO (control group), PRG-N-01 (5 µM), or TEW7197 (5 µM), respectively. After 4 days, the cells were fixed with 70% ethanol and labeled with propidium iodine. These samples were analyzed by FACS for cell-cycle analysis. After 7 days of treatment with DMSO (control group), PRG-N-01, or TEW7197 at the indicated concentration, the cells were fixed with 4% paraformaldehyde and then stained with indicated antibody. A minimum of 10,000 cells were analyzed using an Attune NxT Flow cytometer (Thermo Fisher Scientific, Inc., Rockford, IL, USA).

Example 9: Luciferase Assay

To estimate the transcriptional activity of TGF-β signaling, 3TP-Luc vectors were transfected into cells for 24 hours, and the cells were treated with the indicated chemicals. After washing with wash buffer (Promega, Wisconsin, USA), the cells were lysed using lysis buffer (Promega, Wisconsin, USA). Luciferase activity was measured using a luminometer (MicroDigital, Gyeonggi-do, Korea).

Example 10: Cell Proliferation

Cell growth curves were analyzed by seeding $2\times10^4$ cells/well into a 6-well plate. After the indicated day, the cells were trypsinized and dissociated into single cells. A minimum of 10,000 cells were counted using an Attune NxT flow cytometer (Thermo Fisher Scientific, Inc., Rockford, IL, USA).

Example 11: Microarray Analysis

Total RNA (500 ng) was extracted using an RNAeasy kit (Qiagen). RNA labeling, hybridization on Human Gene 1.0 ST array (Affymetrix), and data analysis were performed using DNA Link (Seoul, Korea). Genes showing at least a 2-fold difference in each cell line were selected for further analysis.

Experimental Example 1: Chemical Screening for RKIP Induction in the Neurofibromatosis Type 2 Cell Line Because RKIP degradation in NF2 cells is clearly known (Mol Cancer Ther 17, 2271-2284, 2018), after first treating 260 novel synthetic compounds, RKIP expression was measured in HEI-193, a human NF2 cell line. It was observed that 14 compounds induced RKIP expression in HEI-193 cells through Western blot (FIGS. 1A and 2). Of these, four compounds suppressed cell viability in both HEI-193 cells and NF2 mouse cells, similar to TEW7197, which is known as a TβR1 kinase inhibitor (FIG. 1B). In addition, SR08002 (renamed Nf-08001) was found as a compound having an inhibitory effect on the binding between TβR1 and RKIP.
[Structure of SR08002 (NF-08001)]

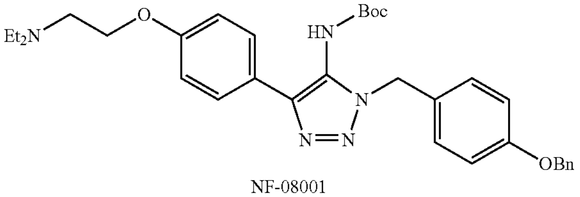

NF-08001

Experimental Example 2: Optimization of NF-08001

Despite the induction of RKIP and anti-proliferating effect in NF2 cells, NF-08001 exhibited normal cytotoxicity as shown in FIG. 3, and thus optimization (alteration) for NF-08001 was required.

Therefore, 39 derivatives for NF-08001 were synthesized, the cell proliferative effect in NF2 cells and normal fibroblasts was examined (FIG. 4), and from these results, it was derived that two compounds (PRG-N-01 and Nf18011) showed obvious antiproliferative effect in NF2 cells without causing toxicity in normal fibroblasts (FIG. 5A). In addition, these compounds induced RKIP expression and inhibited Erk activation (FIG. 6A).

In addition, as a result of examining the effect on the interaction between TβR1 and RKIP, four compounds including PRG-N-01 and Nf18011 inhibited the interaction between TβR1 and RKIP in a dose-dependent manner (FIG. 5B), and PRG-N-01 showed an inhibitory effect even at low concentrations (FIG. 6B). In addition, PRG-N-01 increased RKIP expression in human and mouse NF2 cell lines (FIGS. 5C and 6C).

On the other hand, because TEW7197 was ruled out of drug candidates, owing to TGF-β signal inhibition, the effect of compounds on TGF-β signaling was examined through Smad2/3 phosphorylation and a 3TP-luciferase assay. Unlike TEW7197, these compounds did not disrupt Smad 2/3 phosphorylation and an increase in luciferase activity by reacting with TGF-β (FIGS. 5D and 5E). In addition, the compounds did not alter other signaling cascades, such as IGF-1-induced AKT activation in HEI-193 (FIG. 7A).

Considering the results of such the compound screening and optimization, PRG-N-01 was chosen as a candidate for further analysis (FIG. 7B).

Experimental Example 3: Effect of PRG-N-01 in NF2-Deficient Conditions

To reconfirm the effect of PRG-N-01, the interaction between TβR1 and RKIP was examined. PRG-N-01 interrupted the binding in a dose-dependent manner (FIGS. 8A and 9A). Because the interaction between TβR1 and RKIP occurred under NF2 or TβR2-deficient conditions, it was expected that restoring of NF2 might abolish chemical effects such as RKIP induction, Erk inhibition and antiproliferation, and RKIP induction and p-Erk suppression by PRG-N-01 were observed only in actual mouse schwannoma, but not in normal fibroblasts (FIG. 9B). In addition, no chemical effect (antiproliferating effect, RKIP induction, and p-Erk suppression) was observed in NF2-transfected HEI-193 cells as shown in FIGS. 8B and 8C, and NF2-transfected mouse schwannoma cells as shown in FIGS. 9C and 9D. Of course, NF2 transfection itself increased RKIP expression (FIGS. 8C and 9C). In addition, PRG-N-01 did not inhibit TGF-β signaling even at high concentrations (FIG. 8D).

To examine the more detailed mechanism of action of PRG-N-01, the effect of PRG-N-01 on RKIP mutants was examined. Previous studies have revealed that phosphorylation at the threonine 101 site by TβR1 kinase promotes RKIP destabilization (Mol Cancer Ther 17, 2271-2284, 2018). Although PRG-N-01 induced wild-type RKIP expression, it did not alter the expression of two kinds of RKIP mutants (RKIP T101A; stable form, RKIP T101D; unstable form) (FIG. 8E). From these results, it may be indicated that PRG-N-01 protected RKIP from TβR1-mediated destabilization.

Experimental Example 4: Gene Expression Profile of PRG-N-01-Treated NF2 Cells

To investigate the effect of PRG-N-01 on gene expression profiles, microarray analysis was performed using PRG-N-01-treated HEI-193 cells (FIG. 10A), and the expression of various genes was decreased (Cluster A) or increased (Cluster B) in PRG-N-01-treated HEI-193 cells compared to the control group. Gene ontology (GO) analysis classified the clustered genes into two categories: cell-cycle-related processes, including "cell division", and lipid metabolism-related processes, including "cholesterol biosynthetic process" (FIGS. 10B and 11). Pathway analysis also suggested a similar result, i.e., cell-cycle and steroid pathways (FIGS. 10C and 11). In addition, the cluster of genes that were strikingly upregulated by PRG-N-01 included lipid metabolism-related genes such as PNILPRP3, NR4A2, and ABCA1, whereas cell-cycle-related genes, such as PLK1 and CENPE, were included in most downregulated gene clusters (FIG. 10D). In addition, as a considerably upregulated gene, tenascin C, the readout of canonical TGF-β signaling, was observed, supporting the preliminary result that PRG-N-01 facilitated TGF-β signal activation in HEI-193 cells (Table 1).

| Gene Symbol | Gene Description | Log2Ratio |
|---|---|---|
| SPINK1 | serine peptidase inhibitor, Kazal type 1 | 4.394924 |
| CGB8 | chorionic gonadotropin, beta polypeptide 8 | 3.096694 |
| TNC | tenascin C | 2.869965 |
| PNLIPRP3 | pancreatic lipase-related protein 3 | 2.83996 |
| ATP6V0D2 | ATPase, H+ transporting, lysosomal 38 kDa, V0 subunit d2 | 2.50619 |
| NR4A2 | nuclear receptor subfamily 4, group A, member 2 | 2.409376 |
| ABCA1 | ATP binding cassette subfamily A member 1 | 2.390991 |
| IFI44L | interferon-induced protein 44-like | 2.209413 |
| MMP1 | matrix metallopeptidase 1 | 2.162999 |
| RSAD2 | radical S-adenosyl methionine domain containing 2 | 1.97464 |
| KLHL38 | kelch-like family member 38 | 1.97423 |
| GEM | GTP binding protein overexpressed in skeletal muscle | 1.891961 |
| DDIT3 | DNA-damage-inducible transcript 3 | 1.823283 |
| PDK4 | pyruvate dehydrogenase kinase, isozyme 4 | 1.794382 |
| PLIN2 | perilipin 2 | 1.75132 |
| TNFAIP6 | tumor necrosis factor, alpha-induced protein 6 | 1.733874 |
| OAS1 | 2-5-oligoadenylate synthetase 1 | 1.719042 |
| BIRC3 | baculoviral IAP repeat containing 3 | 1.712554 |
| AKR1B1 | aldo-keto reductase family 1, member B1 (aldose reductase) | 1.669515 |
| BEST1 | bestrophin 1 | 1.660863 |
| ACAT2 | acetyl-CoA acetyltransferase 2 | −2.59115 |
| HIST1H1B | histone cluster 1, H1b | −2.47523 |
| KIF20A | kinesin family member 20A | −2.37763 |
| FABP3 | fatty acid binding protein 3, muscle and heart | −2.27224 |
| DLGAP5 | discs, large (*Drosophila*) homolog-associated protein 5 | −2.24522 |
| HIST1H2AI | histone cluster 1, H2ai | −2.23828 |
| PRR11 | proline rich 11 | −2.20725 |
| HMGCS1 | 3-hydroxy-3-methylglutaryl-CoA synthase 1 (soluble) | −2.18695 |
| UCP2 | uncoupling protein 2 (mitochondrial, proton carrier) | −2.13593 |
| TMSB15A | thymosin beta 15a | −2.09931 |
| OLFML3 | olfactomedin like 3 | −2.09915 |

-continued

| Gene Symbol | Gene Description | Log2Ratio |
|---|---|---|
| CENPE | centromere protein E | −2.05739 |
| HIST1H38 | histone cluster 1, H3b | −2.05646 |
| PLK1 | polo-like kinase 1 | −2.04072 |
| DEPDC1 | DEP domain containing 1 | −2.02617 |
| MSMO1 | methylsterol monooxygenase 1 | −1.98842 |
| MMP2 | matrix metallopeptidase 2 | −1.98701 |
| PBK | PDZ binding kinase | −1.97622 |
| MEST | mesoderm specific transcript | −1.95035 |
| TOP2A | topoisomerase (DNA) II alpha | −1.93127 |

Experimental Example 5: PRG-N-01 Inhibits the Cell Cycle and Promotes Differentiation into Schwann Cells On the basis of gene expression profiling, the cell cycle was monitored after treatment of PRG-N-01, and cell cycle arrest was induced at the G1 phase (FIGS. 12A and 13A). PRG-N-01 treatment completely inhibited cell growth (FIG. 12B) and induced morphological changes (FIGS. 12C and 13B). Because the morphological change by PRG-N-01 was very similar to that of the TEW7197 treated group or NF2-transfected HEI-193, it was expected that PRG-N-01 may induce cell differentiation.

Expression of schwann cell markers as well as cell cycle-related genes was examined, expression of cell cycle-related genes (CDKI, CDK4, CCNB1, and PLK4) was decreased by PRG-N-01 consistent with microarray analysis (FIG. 12D), and in contrast, that of schwann cell markers (PLP, MBP, GFAP MPZ, PMP22, and SOX10) were increased by PRG-N-01 (FIGS. 12D and 13C). In addition, it was observed that the expression of schwann cell marker and TβR2 was increased, but that of SOX2, a stem cell marker, was reduced at the protein level (FIG. 12E).

To re-determine whether PRG-N-01 induces differentiation into schwann cells, the expression of differentiation markers by FACS analysis and IF staining was re-examined. In the FACS analysis, PRG-N-01 clearly increased schwann cell markers compared to TEW7197 (FIG. 12F), and similar results were obtained in IF staining results (FIGS. 12G and 13D). These results indicate that the physiological effect of PRG-N-01 is a cell-cycle arrest and differentiation promoter.

Experimental Example 6: PRG-N-01 Inhibits Stemness of Schwannoma Cells by Inducing RKIP SOX2 is a well-known stem cell factor that maintains stemness under both physiological and pathological conditions, whereas SOX10 orchestrates the differentiation of schwann cells with SOX2, and schwann cells in the NF2-null mouse model showed low levels of SOX10.

In the previous experiment, the induction of SOX10 and reduction of SOX2 were observed by treatment with PRG-N-01. Therefore, the effect of PRG-N-01 on other stem cell factors such as c-Myc, Nanog, and Oct4 was examined, and the expression of these factors was not altered (FIG. 14A). In addition, to test the antitumor effect of PRG-N-01, a tumorsphere formation assay was performed. HEI-193 and mouse schwannoma cells easily formed tumorspheres, and TEW7197 had a weak inhibitory effect on these tumorspheres, while PRG-N-01 obviously inhibited tumorsphere formation (FIGS. 15A and 14B). According to FIGS. 14C and 14D, PRG-N-01 reduced the tumorsphere size as well as the number of tumorsphere. Under these conditions, the expression of stem cell factors (SOX2, c-Myc, Nanog, and Oct4) was downregulated to undetectable levels by treatment with PRG-N-01, whereas SOX10 expression was obviously increased (FIGS. 15B and 14E).

To investigate the molecular mechanism of reduction in SOX2, localization of SOX2 was examined through IF and cell fractionation, and it was revealed that nuclear SOX2 was moved to the cytosol in response to PRG-N-01 and TEW7197 (FIGS. 15C and 15D). A nuclear export inhibition by leptomycin B or a proteasome inhibitor (MG312) blocked the PRG-N-01/TEW7197-induced reduction in SOX2 (FIGS. 14F and 14G). These results indicate that PRG-N-01 promotes SOX2 export and degradation.

In addition, as a result of examining the effect of RKIP on SOX2 reduction and SOX10 induction, ectopic expression of wild-type and stabilized RKIP (T101A) reduced SOX2 expression and RKIP T101A induced SOX10, while RKIP T101D did not reduce SOX2 expression (FIG. 15E). Moreover, si-RKIP abolished PRG-N-01-induced reduction in SOX2 and cytosolic localization (FIG. 15F). These results imply that RKIP is critical for PRG-N-01-induced reduction in SOX2 and increase in SOX10.

To develop a new drug candidate for treating NF2 without disruption of TGF-β signaling, the present inventors monitored the effect of PRG-N-01 on canonical TGF-β signaling cascade, and Smad 2/3 phosphorylation was prolonged by treatment of PRG-N-01 in HEI-193 (FIGS. 16A and 16B). Similar features were observed in RKIP- or NF2-transfected HEI-193 cells (FIGS. 16C and 16D). These results indicate that the effect of PRG-N-01 on TGF-β signaling was very similar to the NF2 restoration induction feature.

Experimental Example 7: PRG-N-01 has an Antitumor Effect In Vivo

To examine the in vivo effect of PRG-N-01, NF2 model mouse-derived schwannoma cells were allografted to 8-week-old mice, and PRG-N-01 was administered by intraperitoneal injection (20 mg/kg, 3 times a week). Treatment with PRG-N-01 inhibited tumor growth (FIGS. 17A and 18A). Tumor size and weight were obviously suppressed (FIGS. 17B and 17C).

Injection of PRG-N-01 into normal mice at a dose of 200 mg/kg that is 10 times higher than the therapeutic dose did not change the body weight (FIG. 18B), indicating that PRG-N-01 did not cause severe toxicity.

In addition, as a result of analyzing the expression of RKIP and related genes in tumors, induction of RKIP, PRG-N-01-treated tumor tissues showed induction of RKIP, schwann cell markers (PLP, MBP, and MPZ), and SOX10 at the protein level (FIG. 17D). RT-PCR analysis also showed induction of schwann cell markers and SOX10 and the reduction in SOX2 (FIG. 17E).

Considering in vitro and in vivo results, it was determined that PRG-N-01 is a potential drug candidate for NF2-derived schwannoma.

Having described in detail on a specific part of the present disclosure above, it is clear for those skilled in the art that such specific description is only a desirable example embodiment, and the scope of the present disclosure is not limited thereby. Therefore, the substantive scope of the present disclosure will be defined by the attached claims and their equivalents.

The scope of the present disclosure is indicated by the claims to be described below, and the meaning and scope of the claims and all alterations or modified forms derived from the equivalence concept thereof should be construed as being included in the scope of the present disclosure.

The invention claimed is:

1. A compound selected from a compound represented by the following Chemical Formula 1, a pharmaceutically acceptable salt thereof, a solvate thereof, or a stereoisomer thereof:

[Chemical Formula 1]

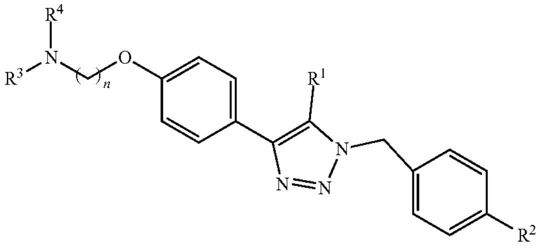

wherein, in the Chemical Formula 1, $R^1$ is $NR^5R^6$ or CN, $R^5$ or $R^6$ is the same or different respectively and hydrogen or (C1~C4)alkyl, $R^2$ is halo, (C1~C4)alkyl, or (C1~C4)alkoxy, $R^3$ or $R^4$ is the same or different respectively and hydrogen, (C1~C4)alkyl, or (C1~C4)alkoxy, and n is an integer of 0 to 3.

2. The compound of claim 1, wherein, in the compound represented by Chemical Formula 1, $R^1$ is $NH_2$ or $NR^5R^6$, $R^5$ or $R^6$ is the same or different respectively and (C1~C2) alkyl, $R^2$ is (C1~C4)alkoxy, $R^3$ or $R^4$ is the same or different respectively and (C1~C4)alkyl, and n is an integer of 1 to 2.

3. The compound of claim 1, wherein, in the compound represented by Chemical Formula 1, $R^1$ is $NH_2$, $R^2$ is (C1~C2)alkoxy, $R^3$ and $R^4$ are (C1~C2)alkyl, and n is an integer of 1 to 2.

4. A method of preventing or treating neurofibromatosis type 2 (NF2) syndrome in a subject, comprising:

administering a pharmaceutical composition comprising a compound selected from a compound represented by the following Chemical Formula 1, a pharmaceutically acceptable salt thereof, a solvate thereof, or a stereoisomer thereof to the subject:

[Chemical Formula 1]

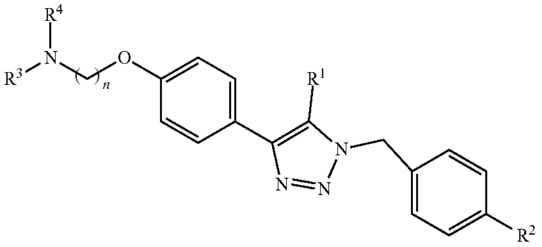

wherein, in the Chemical Formula 1, $R^1$ is $NR^5R^6$ or CN, $R^5$ or $R^6$ is the same or different respectively and hydrogen or (C1~C4)alkyl, $R^2$ is halo, (C1~C4)alkyl, or (C1~C4)alkoxy, $R^3$ or $R^4$ is the same or different respectively and hydrogen, (C1~C4)alkyl, or (C1~C4)alkoxy, and n is an integer of 0 to 3.

5. A method of preventing or ameliorating neurofibromatosis type 2 (NF2) syndrome in a subject, comprising:

administering a health food composition comprising a compound selected from a compound represented by the following Chemical Formula 1, a pharmaceutically acceptable salt thereof, a solvate thereof, or a stereoisomer thereof to the subject:

[Chemical Formula 1]

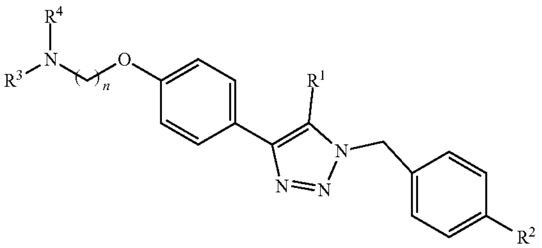

wherein, in the Chemical Formula 1, $R^1$ is $NR^5R^6$ or CN, $R^5$ or $R^6$ is the same or different respectively and hydrogen or (C1~C4)alkyl, $R^2$ is halo, (C1~C4)alkyl, or (C1~C4)alkoxy, $R^3$ or $R^4$ is the same or different respectively and hydrogen, (C1~C4)alkyl, or (C1~C4)alkoxy, and n is an integer of 0 to 3.

* * * * *

SEQUENCE LISTING

<160> NUMBER OF SEQ ID NOS: 21

<210> SEQ ID NO 1
<211> LENGTH: 57
<212> TYPE: DNA
<213> ORGANISM: Artificial Sequence
<220> FEATURE:
<223> OTHER INFORMATION: si-RKIP

<400> SEQUENCE: 1
caccagcatt tcgtgggatg gtctttcaag agaagaccat cccacgaaat gctggtg 57

<210> SEQ ID NO 2
<211> LENGTH: 20
<212> TYPE: DNA
<213> ORGANISM: Artificial Sequence
<220> FEATURE:
<223> OTHER INFORMATION: hSOX2 (Forward)

<400> SEQUENCE: 2
tcgcagacct acatgaacgg 20

<210> SEQ ID NO 3
<211> LENGTH: 20
<212> TYPE: DNA
<213> ORGANISM: Artificial Sequence
<220> FEATURE:
<223> OTHER INFORMATION: hSOX2 (Reverse)

<400> SEQUENCE: 3
acatgtgaag tctgctgggg 20

<210> SEQ ID NO 4
<211> LENGTH: 21
<212> TYPE: DNA
<213> ORGANISM: Artificial Sequence
<220> FEATURE:
<223> OTHER INFORMATION: hSOX10 (Forward)

<400> SEQUENCE: 4
catggagacc tttgatgtgg c 21

<210> SEQ ID NO 5
<211> LENGTH: 21
<212> TYPE: DNA
<213> ORGANISM: Artificial Sequence
<220> FEATURE:
<223> OTHER INFORMATION: hSOX10 (Reverse)

<400> SEQUENCE: 5
tcagagtagt caaactgggg g 21

<210> SEQ ID NO 6
<211> LENGTH: 20
<212> TYPE: DNA
<213> ORGANISM: Artificial Sequence
<220> FEATURE:
<223> OTHER INFORMATION: hMBP (Forward)

<400> SEQUENCE: 6
caagtaccat ggaccatgcc 20

<210> SEQ ID NO 7
<211> LENGTH: 21
<212> TYPE: DNA
<213> ORGANISM: Artificial Sequence -continued
<220> FEATURE:
<223> OTHER INFORMATION: hMBP (Reverse)

<400> SEQUENCE: 7
tttatagtcg gacgctctgc c 21

<210> SEQ ID NO 8
<211> LENGTH: 21
<212> TYPE: DNA
<213> ORGANISM: Artificial Sequence
<220> FEATURE:
<223> OTHER INFORMATION: hMPZ (Forward)

<400> SEQUENCE: 8
caaccctaca ttgacgaggt g 21

<210> SEQ ID NO 9
<211> LENGTH: 21
<212> TYPE: DNA
<213> ORGANISM: Artificial Sequence
<220> FEATURE:
<223> OTHER INFORMATION: hMPZ (Reverse)

<400> SEQUENCE: 9
cactgacagc tttggtgctt c 21

<210> SEQ ID NO 10
<211> LENGTH: 21
<212> TYPE: DNA
<213> ORGANISM: Artificial Sequence
<220> FEATURE:
<223> OTHER INFORMATION: hPMP22 (Forward)

<400> SEQUENCE: 10
gcaatggaca cgcaactgat c 21

<210> SEQ ID NO 11
<211> LENGTH: 21
<212> TYPE: DNA
<213> ORGANISM: Artificial Sequence
<220> FEATURE:
<223> OTHER INFORMATION: hPMP22 (Reverse)

<400> SEQUENCE: 11
cgaaaccgta ggagtaatcc g 21

<210> SEQ ID NO 12
<211> LENGTH: 21
<212> TYPE: DNA
<213> ORGANISM: Artificial Sequence
<220> FEATURE:
<223> OTHER INFORMATION: mSOX2 (Forward)

<400> SEQUENCE: 12
aggataagta cacgcttccc g 21

<210> SEQ ID NO 13
<211> LENGTH: 20
<212> TYPE: DNA
<213> ORGANISM: Artificial Sequence
<220> FEATURE:
<223> OTHER INFORMATION: mSOX2 (Reverse)

<400> SEQUENCE: 13
taggacatgc tgtaggtggg 20

-continued

<210> SEQ ID NO 14
<211> LENGTH: 21
<212> TYPE: DNA
<213> ORGANISM: Artificial Sequence
<220> FEATURE:
<223> OTHER INFORMATION: mSOX10 (Forward)

<400> SEQUENCE: 14
actacaagta ccaacctcgg c 21

<210> SEQ ID NO 15
<211> LENGTH: 20
<212> TYPE: DNA
<213> ORGANISM: Artificial Sequence
<220> FEATURE:
<223> OTHER INFORMATION: mSOX10 (Reverse)

<400> SEQUENCE: 15
gttggacatt acctcgtggc 20

<210> SEQ ID NO 16
<211> LENGTH: 20
<212> TYPE: DNA
<213> ORGANISM: Artificial Sequence
<220> FEATURE:
<223> OTHER INFORMATION: mMBP (Forward)

<400> SEQUENCE: 16
ttctttagcg gtgacagggg 20

<210> SEQ ID NO 17
<211> LENGTH: 21
<212> TYPE: DNA
<213> ORGANISM: Artificial Sequence
<220> FEATURE:
<223> OTHER INFORMATION: mMBP (Reverse)

<400> SEQUENCE: 17
taaatctgct gagggacagg c 21

<210> SEQ ID NO 18
<211> LENGTH: 22
<212> TYPE: DNA
<213> ORGANISM: Artificial Sequence
<220> FEATURE:
<223> OTHER INFORMATION: mMPZ (Forward)

<400> SEQUENCE: 18
ctgctccttc tggtccagtg aa 22

<210> SEQ ID NO 19
<211> LENGTH: 22
<212> TYPE: DNA
<213> ORGANISM: Artificial Sequence
<220> FEATURE:
<223> OTHER INFORMATION: mMPZ (Reverse)

<400> SEQUENCE: 19
aggttgtccc ttggcatagt gg 22

<210> SEQ ID NO 20
<211> LENGTH: 22
<212> TYPE: DNA
<213> ORGANISM: Artificial Sequence
<220> FEATURE:
<223> OTHER INFORMATION: mPMP22 (Forward)

-continued

<400> SEQUENCE: 20
cgtccaacac tgctactcct ca 22

<210> SEQ ID NO 21
<211> LENGTH: 22
<212> TYPE: DNA
<213> ORGANISM: Artificial Sequence
<220> FEATURE:
<223> OTHER INFORMATION: mPMP22 (Reverse)

<400> SEQUENCE: 21
gcctttggtg agagtgaaga gc 22